United States Patent [19]

Kreutter et al.

[11] Patent Number: 5,627,200

[45] Date of Patent: May 6, 1997

[54] β₃-ADRENOCEPTOR AGONISTS AND ANTAGONISTS FOR THE TREATMENT OF INTESTINAL MOTILITY DISORDERS, DEPRESSION, PROSTATE DISEASE AND DYSLIPIDEMIA

[75] Inventors: David K. Kreutter, Madison; Robert L. Dow, Waterford, both of Conn.

[73] Assignee: Pfizer Inc, New York, N.Y.

[21] Appl. No.: 312,027

[22] Filed: Sep. 26, 1994

[51] Int. Cl.$^6$ ............ A61K 31/38; A61K 31/415; A61K 31/42; A61K 31/425

[52] U.S. Cl. ............ 514/367; 514/2; 514/256; 514/269; 514/272; 514/273; 514/274; 514/338; 514/339; 514/255; 514/375; 514/397; 514/398; 514/399; 514/443; 514/469; 514/470

[58] Field of Search ............ 514/365, 372, 514/443, 469, 2, 255, 256, 269, 272, 273, 274, 338, 339, 367, 375, 397, 398, 399, 470

[56] References Cited

U.S. PATENT DOCUMENTS

| | | | |
|---|---|---|---|
| 4,309,433 | 1/1982 | Smith et al. | 424/319 |
| 4,339,333 | 7/1982 | Ainsworth et al. | 424/309 |
| 4,341,793 | 7/1982 | Ferris | 424/279 |
| 4,382,958 | 5/1983 | Duckworth | 424/330 |
| 4,396,627 | 8/1983 | Ainsworth et al. | 424/309 |
| 4,432,993 | 2/1984 | Ferris | 424/285 |
| 4,607,033 | 8/1986 | Cantello | 514/233 |
| 4,654,371 | 3/1987 | Ainsworth et al. | 514/555 |
| 4,886,814 | 12/1989 | Reiffen et al. | 514/326 |
| 5,061,727 | 10/1991 | Bloom et al. | 514/465 |

FOREIGN PATENT DOCUMENTS

| | | |
|---|---|---|
| 140359 | 5/1985 | European Pat. Off. . |
| 170135 | 2/1986 | European Pat. Off. . |
| 254532 | 1/1988 | European Pat. Off. . |
| 516349 | 12/1992 | European Pat. Off. . |
| 611003 | 8/1994 | European Pat. Off. . |

OTHER PUBLICATIONS

Giudice et al., *Life Science*, 44, 19, 1411–1417 (1989).

Simiand et al., *Eur. J. of Pharmacol.*, 219, 193–201 (1992).

Krief et al., *J. Clin. Invest.*, 91, 344–349 (1993).

D.T. Taneja, et al., entitled "*Evidence for a Noradrenergic Innervation to 'Atypical' Beta Adrenoceptors (or Putative Beta–3 Adrenoceptors) in the Ileum of Guinea Pig*". The Journal of Pharmacology and Experimental Therapeutics: 260, 1, 192–200 (1992).

Luciano Manara, et al., entitled "*Inhibition of Rat Colonic Motility and Cardiovascular Effects of New Gut–Specific Beta–Adrenergic Phenylethanolaminotetralines*", Life Sciences, 44, 1411–1417, (1989).

Peter E. Keane, et al., entitled "*Antidepressant Profile in Rodens of SR 58611A, a New Selective Agonist for Atypical β–adrenoceptors*", European Journal of Pharmacology, 219, 193–201, (1992).

Laurent J. Emorine, et al., entitled "*Tissue Distribution of β3–Adrenergic Receptor mRNA in Man*", J. Clin. Invest., 91, 344–349, (1993).

*Primary Examiner*—Phyllis G. Spivack
*Attorney, Agent, or Firm*—Peter C. Richardson; Paul H. Ginsburg; Garth C. Butterfield

[57] ABSTRACT

This invention relates to methods for treating intestinal motility disorders, intestinal ulcerations, including inflammatory bowel disease, ulcerative colitis, Crohn's disease and proctitis, and gastrointestinal ulcerations, depression, prostate disease and dyslipidemia by administering a β₃-adrenoceptor antagonist or agonist.

6 Claims, No Drawings

$\beta_3$-ADRENOCEPTOR AGONISTS AND ANTAGONISTS FOR THE TREATMENT OF INTESTINAL MOTILITY DISORDERS, DEPRESSION, PROSTATE DISEASE AND DYSLIPIDEMIA

BACKGROUND OF THE INVENTION

This invention relates to methods for treating or preventing intestinal motility disorders, depression, prostate disease and dyslipidemia by administering a $\beta_3$-adrenoceptor antagonist or agonist. This invention also relates to pharmaceutical compositions for treating or preventing intestinal motility disorders, depression, prostate disease and dyslipidemia comprising a $\beta_3$-adrenoceptor antagonist or agonist.

$\beta$-Adrenergic receptors have been categorized into $\beta_1$, $\beta_2$ and $\beta_3$-subtypes. Agonists of $\beta$-receptors promote the activation of adenylyl cyclase. Activation of $\beta_1$-receptors invokes increases in heart rate while activation of $\beta_2$-receptors induces relaxation of skeletal muscle tissue which produces a drop in blood pressure and the onset of smooth muscle tremors. Activation of $\beta_3$-receptors is known to stimulate lipolysis (the breakdown of adipose tissue triglycerides to glycerol and free fatty acids), and thereby promote the loss of fat mass. Compounds that stimulate $\beta_3$-receptors are therefore useful as anti-obesity agents. In addition, compounds which are $\beta_3$-adrenoceptor agonists have hypoglycemic or anti-diabetic activity, but the mechanism of this effect is unknown.

Until recently $\beta_3$-adrenoceptors were thought to be found predominately in adipose tissue. $\beta_3$-receptors are now known to be located in such diverse tissues as the intestine and the brain. *J. Clin. Invest.*, 91, 344 (1993). Stimulation of the $\beta_3$-receptor has been demonstrated to cause relaxation of smooth muscle in colon and trachea. *Life Sciences*, 44, 19, 1411 (1989); *Br. J. Pharm.*, 112, 55 (1994). For example, stimulation of $\beta_3$-receptors has been found to induce relaxation of histamine-contracted guinea pig ileum, *J. Pharm. Exp. Ther.*, 260, 1, 192 (1992).

It has now been found that there is expression of the $\beta_3$-receptor in human prostate. Antagonism or agonism of these receptors should result in relaxation of prostate smooth muscle and that $\beta_3$-agonists and antagonists should be useful for the treatment or prevention of prostate disease.

Administration of N-[(2S)-7-carbethoxymethoxy-1,2,3,4-tetrahydronaphth-2-yl]-(2R)-2-hydroxy-2-(3-chlorophenyl)-ethanamine hydrochloride, a $\beta_3$-agonist, has been reported to demonstrate activity in rodent models of depression, *Europ. J. Pharm.*, 219, 193 (1992).

N-[2-(4-carbomethoxymethoxyphenyl)-1-methylethyl]-2-hydroxy-2-(3-chlorophenyl)ethanamine reduces plasma triglycerides and fatty acids in genetic animal models of obesity and diabetes and therefore will be useful for the treatment and prevention of dyslipidemia.

U.S. patent application Ser. No. 08/076,026, filed Jun. 14, 1993, discloses the use of compounds of the formula I, described below, for the treatment or prevention of diabetes, hypoglycemia, and weight loss.

U.S. Pat. No. 4,338,333, issued Jul. 6, 1982, refers to ethanamine derivatives including the compound of formula K, described below, which possess antiobesity and antihyperglycaemic activity.

U.S. Pat. No. 5,061,727, issued Oct. 29, 1991, refers to substituted 5-(2-(2-aryl-2-hydroxyethyl)-amino)-propyl)-1,3-benzodioxoles including the compound of formula J,  described below, which possess antidiabetic, antihyperglycemic and antiobesity properties.

European Patent publication 516,349, published Dec. 2, 1992, refers to 2-hydroxyphenethyl amines including the compound of formula L, described below, which possess antiobesity, hypoglycemic and related utilities.

SUMMARY OF THE INVENTION

This invention relates to a method for treating or preventing prostate disease in a mammal, preferably a human, comprising administering to a mammal in need of such treatment or prevention a $\beta_3$-adrenoceptor antagonizing or agonizing effective amount of a $\beta_3$-adrenoceptor antagonist or agonist or a pharmaceutically acceptable salt or prodrug thereof.

This invention also relates to a pharmaceutical composition for treating or preventing prostate disease in a mammal, preferably a human, comprising an amount of a $\beta_3$-adrenoceptor antagonist or agonist effective in antagonizing or agonizing the $\beta_3$-andrenoceptor, or a pharmaceutically acceptable salt or prodrug thereof, and a pharmaceutically acceptable carrier.

The present invention relates to a method of treating or preventing a condition selected from the group consisting of intestinal motility disorders such as irritable bowel syndrome, peptic ulceration, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, depression, prostate disease, neurogenetic inflammation and dyslipidemia in a mammal, preferably a human, comprising administering to a mammal in need of such treatment or prevention a $\beta_3$-adrenoceptor antagonizing or agonizing effective amount of either (a) an amount of a compound of the formula

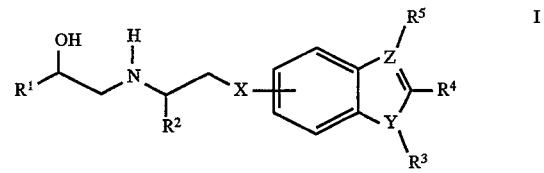

wherein $R^1$ is phenyl, —$(CH_2)_n$—O-phenyl or thiazolyl, wherein said phenyl, the phenyl moiety of said —$(CH_2)_n$—O-phenyl and said thiazolyl may optionally be substituted with one or more substituents, preferably from one to three substituents, independently selected from hydrogen, $(C_1-C_6)$alkyl optionally substituted with one or more halo atoms, preferably from one to three halo atoms, hydroxy, $(C_1-C_6)$alkoxy optionally substituted with one or more halo atoms, preferably from one to three halo atoms, $(C_1-C_6)$alkylthio, fluoro, chloro, bromo, iodo, nitro and cyano;

$R^2$ is hydrogen or $(C_1-C_6)$alkyl optionally substituted with one or more halo atoms, preferably from one to three halo atoms;

$R^3$ is hydrogen, —$(CH_2)_n$-phenyl, —$(C_1-C_{10})$alkyl, —$(CH_2)_n$—$NR^7R^8$, —$(CH_2)_n$—$CO_2R^{11}$,

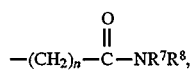

$-(CH_2)_n-OR^{11}$, $-(CH_2)_n-SO_3R^{11}$, $-(CH_2)_n-SO_2-(C_1-C_6)alkyl$, $-(CH_2)_n-SO_2NR^7R^8$, or a heterocycle selected from $-(CH_2)_n$-pyridyl, $-(CH_2)_n$-pyrimidyl, $-(CH_2)_n$-pyrazinyl, $-(CH_2)_n$-isoxazolyl, $-(CH_2)_n$-oxazolyl, $-(CH_2)_n$-thiazolyl, $-(CH_2)_n$-(1,2,4-oxadiazolyl), $-(CH_2)_n$-imidazolyl, $-(CH_2)_n$-triazolyl and $-(CH_2)_n$-tetrazolyl, wherein one of the ring nitrogen atoms of said $-(CH_2)_n$-imidazolyl, $-(CH_2)_n$-triazolyl or $-(CH_2)_n$-tetrazolyl may optionally be substituted by $(C_1-C_6)$alkyl optionally substituted with one or more halo atoms, preferably from one to three halo atoms, and wherein each of said heterocycles may optionally be substituted on one or more of the ring carbon atoms by $(C_1-C_6)$alkyl optionally substituted with one or more halo atoms, preferably from one to three halo atoms, halo, nitro, cyano, $-(CH_2)_n-NR^7R^8$, $-(CH_2)_n-CO_2R^{11}$,

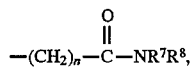

$-(CH_2)_n-OR^{11}$, $-(CH_2)_n-SO_3R^{11}$, $-(CH_2)_n-SO_2-(C_1-C_6)alkyl$, or $-(CH_2)_n-SO_2NR^7R^8$, and wherein the phenyl moiety of said $(CH_2)_n$-phenyl may optionally be substituted with one or more substituents, preferably one to three substituents, independently selected from $(C_1-C_6)$alkyl optionally substituted with one or more halo atoms, preferably from one to three halo atoms, hydroxy, $(C_1-C_6)$ alkoxy optionally substituted with one or more halo atoms, preferably from one to three halo atoms, $(C_1-C_6)$alkylthio, fluoro, chloro, bromo, iodo, cyano, nitro, $-(CH_2)_n-NR^7R^8$, $-(CH_2)_n-CO_2R^2$,

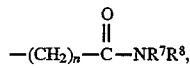

$-(CH_2)_n-OR^{11}$, $-(CH_2)_n-SO_3R^{11}$, $-(CH_2)_n-SO_2-(C_1-C_6)alkyl$, and $-(CH_2)_n-SO_2NR^7R^8$;

$R^4$ is $-(CH_2)_n-CN$, $-(CH_2)_nCO_2R^{11}$, $-(CH_2)_n-SO_3R^{11}$, $-(CH_2)_n-SO_2-(C_1-C_6)alkyl$, $-(CH_2)_n-SO_2-NR^7R^8$, $-(CH_2)_nCH_2OH$ optionally substituted with a suitable protecting group (e.g., benzyl ester and t-butyl ester), $-(CH_2)_n-CHO$, $-(CH_2)_n-C(=O)R^{11}$, $-(CH_2)_n-C(=O)NR^7R^8$, or a heterocycle selected from $-(CH_2)_n$-thiazolyl, $-(CH_2)_n$-oxazolyl, $-(CH_2)_n$-imidazolyl, $-(CH_2)_n$-triazolyl, $-(CH_2)_n$-1,2,4-oxadiazolyl, $-(CH_2)_n$-isoxazolyl, $-(CH_2)_n$-tetrazolyl and $-(CH_2)_n$-pyrazolyl; wherein one of the ring nitrogen atoms of said $-(CH_2)_n$-imidazolyl, $-(CH_2)_n$-triazolyl and $-(CH_2)_n$-tetrazolyl may optionally be substituted by $(C_1-C_6)$alkyl optionally substituted with one or more halo atoms, preferably from one to three halo atoms; wherein each of said heterocycles may optionally be substituted on one or more of the the ring carbon atoms by hydrogen, $(C_1-C_6)$alkyl optionally substituted with one or more halo atoms, preferably from one to three halo atoms, $-(CH_2)_n-NR^7R^8$, $-(CH_2)_n-CO_2R^{11}$, halo, nitro, cyano,

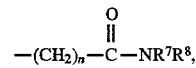

$-(CH_2)_n-OR^{11}$, $-(CH_2)_n-SO_3R^{11}$, $-(CH_2)_n-SO_2-(C_1-C_6)alkyl$, or $-(CH_2)_n-SO_2NR^7R^8$;

$R^5$ is hydrogen or $(C_1-C_6)$alkyl optionally substituted with one or more halo atoms, preferably from one to three halo atoms;

each $R^7$ and each $R^8$ is selected independently of any other $R^7$ and $R^8$ in the same molecule, and is selected from the group consisting of hydrogen, $(C_1-C_6)$ alkyl, $(C_1-C_8)$alkoxy$(C_1-C_6)$alkyl or $(C_3-C_8)$ cycloalkyl, or $R^7$ and $R^8$, when attached to the same nitrogen atom, together with the nitrogen to which they are attached, form a saturated heterocyclic ring having from 3 to 7 carbon atoms wherein one of said carbon atoms may optionally be replaced by oxygen, nitrogen or sulfur;

$R^{11}$, wherever it occurs, is selected independently from any other $R^{11}$ in the same molecule and is selected from hydrogen and $(C_1-C_6)$ alkyl optionally substituted with one or more halo atoms, preferably from one to three halo atoms;

n is an integer from zero to six;

X is a direct link, oxygen or sulfur;

Y is oxygen, nitrogen or sulfur; and

Z is carbon or nitrogen;

with the proviso that: (i) when Y is oxygen or sulfur, $R^3$ is absent, and (ii) when Z is nitrogen, $R^5$ is absent;

or a pharmaceutically acceptable salt or prodrug thereof, that is effective in treating or preventing such condition;

(b) an amount of a compound of the formula

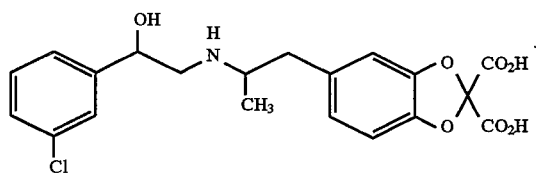

or a pharmaceutically acceptable salt or prodrug thereof, that is effective in treating or preventing such condition;

(c) an amount of a compound of the formula

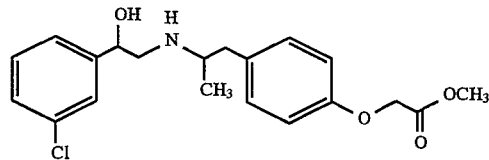

or a pharmaceutically acceptable salt or prodrug thereof, that is effective in treating or preventing such condition with the proviso that the compound of formula K is excluded from the treatment or prevention dyslipidemia; or (d) an amount of a compound of the formula:

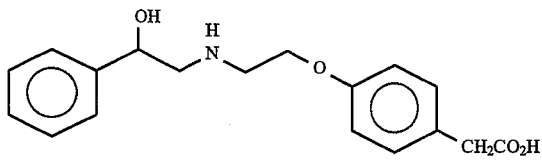
L or a pharmaceutically acceptable salt or prodrug thereof, that is effective in treating or preventing such condition.

The present invention also relates to a pharmaceutical composition for treating or preventing a condition selected from the group consisting of intestinal motility disorders such as irritable bowel syndrome, peptic ulceration, esophagitis, gastritis and duodenitis, (including that induced by H. pylori), intestinal ulcerations (including inflammatory bowel disease, ulcerative colitis, Crohn's disease and proctitis) and gastrointestinal ulcerations, depression, prostate disease, neurogenetic inflammation and dyslipidemia in a mammal, comprising a β-adrenoceptor antagonizing or agonizing effective amount of a compound of formula I, J, K or L, as defined above with the proviso that the compound of formula K is excluded from the treatment or prevention dyslipidemia, or a pharmaceutically acceptable prodrug of such compound, or a pharmaceutically acceptable salt of such compound or prodrug that is effective in treating or preventing such condition, and a pharmaceutically acceptable carrier.

Preferred embodiments of the present invention include pharmaceutical compositions comprising and methods of administering the following compounds of formula I, or pharmaceutically acceptable salts or prodrugs of these compounds:

1-(5-(2(2(S)-hydroxy-3-phenoxy-propylamino)-ethoxy)-benzofuran-2-yl)-ethanone, 1-(2-(2-isoxazol-3-yl-benzofuran-5-yloxy)-ethylamino)-3-phenoxy-propan-2(S)-ol, 1-(2-(2-(5-methyl-isoxazol-3-yl)-benzofuran-5-yloxy)-ethylamino)-3-phenoxy-propan-2(S)-ol, 1-(2-(2-(2-methyl-thiazol-4-yl)-benzofuran-5-yloxy)-ethylamino)-3-phenoxy-propan-2(S)-ol, 1-(2-(2-(5-methyl-(1,2,4)-oxadiazol-3-yl)-benzofuran-5-yloxy)-ethylamino)-3-phenoxy-propan-2(S)-ol, 1-(2-(2-(1,2,4)-oxadiazol-3-yl)-benzofuran-5-yloxy)-ethylamino)-3-phenoxy-propan-2(S)-ol, 1-benzyl-5-(2(R)-(2-(3-chloro-phenyl)-2(R)-hydroxy-ethylamino)-propyl)-1H-indole-2-carboxylic acid methyl ester, 1-benzyl-5-(2(R)-2-(3-chloro-phenyl)-2(R)-hydroxy-ethylamino)-propyl)-1H-indole-2-carboxylic acid, 1-benzyl-5-(2(R,S)-(2(S)-hydroxy-3-phenoxy-propylamino)-propyl)-1H-indole-2-carboxylic acid ethyl ester, 1-benzyl-5-(2(R,S)-(2S)-hydroxy-3-phenoxy-propylamino)-propyl)-1H-indole-2-carboxylic acid, 5-(2(R,S)-(2-(3-chloro-phenyl)-2(R)-hydroxy-ethylamino)-propyl)-1-(4-dimethylsulfamoyl-benzyl)-1H-indole-2-carboxylic acid ethyl ester, 5-(2-(R,S)(2-(3-chloro-phenyl)-2(R)-hydroxy-ethylamino)-propyl)-1-(4-dimethylsulfamoyl-benzyl)-1H-indole-2-carboxylic acid, 1-(4-dimethylsulfamoyl-benzyl)-5-(2(R,S)-(2(S)-hydroxy-3-phenoxy-propylamino)-propyl)-1H-indole-2-carboxylic acid ethyl ester, 1-(4-dimethylsulfamoyl-benzyl)-5-(2(S)-(2(S)-hydroxy-3-phenoxy-propylamino-propyl-1H-indole-2-carboxylic acid, 5-(2(R,S)-(2-(3-chloro-phenyl)-2(R)-hydroxy-ethylamino)-propyl)-1-(4-methanesulfonylamino-benzyl)-1H-indole-2-carboxylic acid ethyl ester, 5-(2(R,S)-(2(3-chloro-phenyl)-2-(R)-hydroxy-ethylamino)-propyl)-1-(4-methanesulfonylamino-benzyl)-1H-indole-2-carboxylic acid, 5-(2(R,S)-(2(S)-hydroxy-3-phenoxy-propylamino)-propyl-1-(4-methanesulfonyl-benzyl)-1H-indole-2-carboxylic acid ethyl ester, 5-(2(R,S)-(2(S)-hydroxy-3-phenoxy-propylamino)-propyl)-1-(4-methanesulfonylamino-benzyl)-1H-indole-2-carboxylic acid, 5-(2(R,S)-(2(R,S)-6-amino-pyridin-3-yl)-2-hydroxy-ethylamino)-propyl)-1-benzyl-1H-indole-2-carboxylic acid ethyl ester, and 5-(2(R,S)-(2(R,S)-6-amino-pyridin-3-yl)-2-hydroxy-ethylamino)-propyl)-1-benzyl-1H-indole-2-carboxylic acid.

As indicated above, this invention also encompasses pharmaceutical compositions containing and methods of treating or preventing comprising administering prodrugs of compounds of the formula I, J, K and L. Compounds of formula I, J, K, or L having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include compounds of formula I in which the secondary amine and its β-hydroxy when taken together form a group of the formula

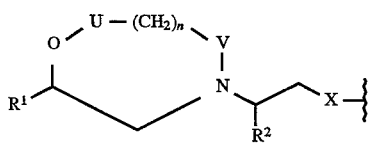
XIX wherein n, $R^1$, $R^2$ and X are as defined in formula I and U and V are independently carbonyl, methylene, $SO_2$ or $SO_3$, wherein methylene is optionally substituted with hydroxy. Prodrugs also include compounds of formula J, K, and L which also contain a secondary amine and a β-hydroxy group that can form an analogous group to formula XIX.

As indicated above, this invention also encompasses pharmaceutical composition containing and methods of treating or preventing comprising administering pharmaceutically acceptable salts of compounds or prodrugs of formula I, J, K and L. The acids that may be used to prepare pharmaceutically acceptable acid addition salts of those compounds of formulae I, J, K and L that are basic in nature are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzene-sulfonate, p-toluenesulfonate and pomoate [i.e., 1,1'-methylene-bis-(2-hydroxy-3-naphthoate)] salts. The chemical bases that may be used as reagents to prepare pharmaceutically acceptable base salts of those compounds of formulae I, J, K and L that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The term "halo", as used herein unless otherwise indicated, includes chloro, fluoro, bromo and Iodo.

The term "alkyl" as used herein, unless otherwise indicated, includes saturated monovalent hydrocarbon radicals having straight, branched or cyclic moieties or The term "alkoxy", as used herein, includes O-alkyl groups wherein "alkyl" is defined as above.

The term "one or more substituents," as used herein, includes from one to the maximum number of substituents possible based on the number of available bonding sites.

The compounds of the formula I, J, K and L have chiral centers and therefore exist in different enantiomeric forms. This invention relates to all optical isomers and all stereoisomers of compounds of the formula I, J, K or L, and mixtures thereof.

DETAILED DESCRIPTION OF THE INVENTION

The processes and products of the present invention are illustrated in the following reaction schemes. Except where otherwise indicated, in the reaction scheme and discussion that follow, formulas I, II, III, IV, and V, and V, and substituents $R^1$, $R^2$, $R^3$, $R^4$, $R^5$, $R^6$, $R^7$, $R^8$, $R^{10}$, X and halogen are defined as above.

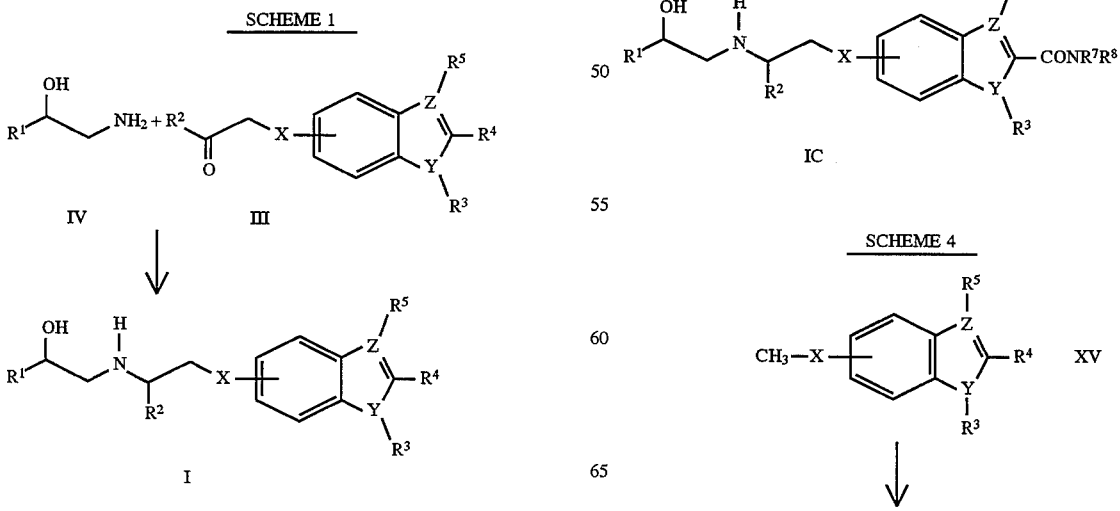

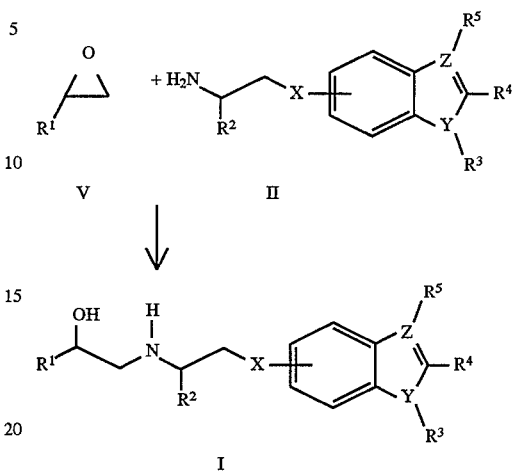

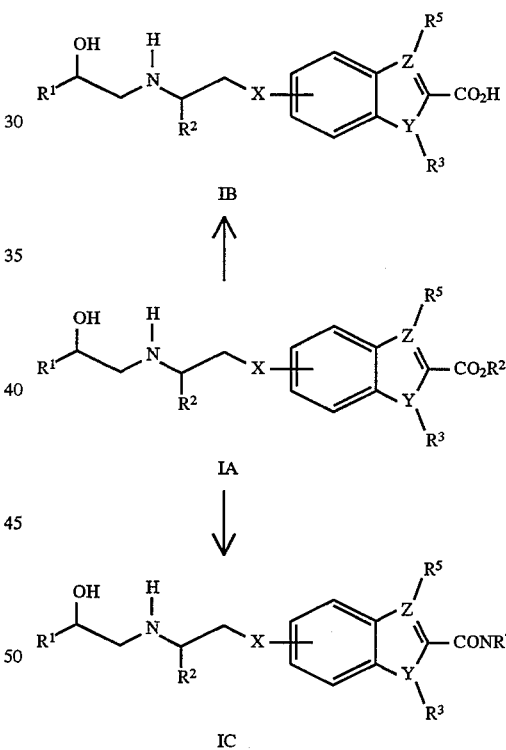

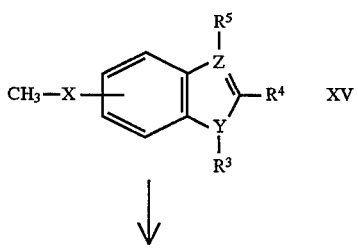

5,627,200
9
-continued
SCHEME 4
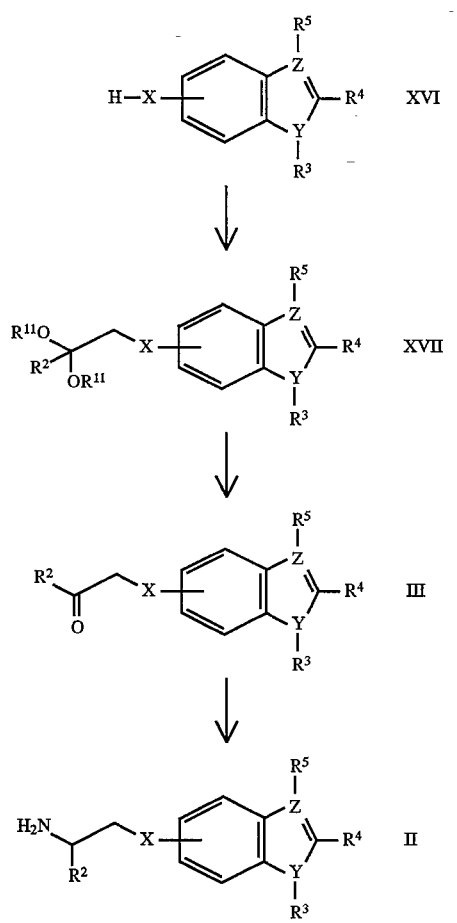
SCHEME 5
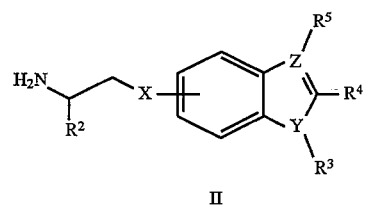
SCHEME 5
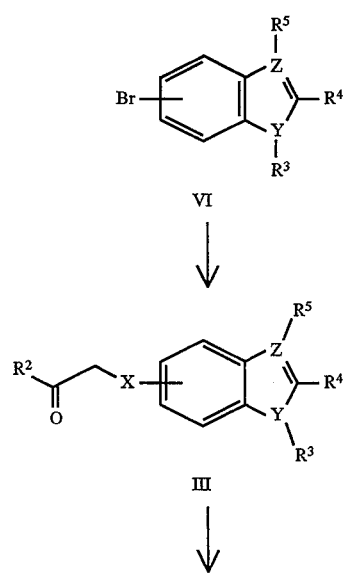
10
-continued
SCHEME 5
SCHEME 6
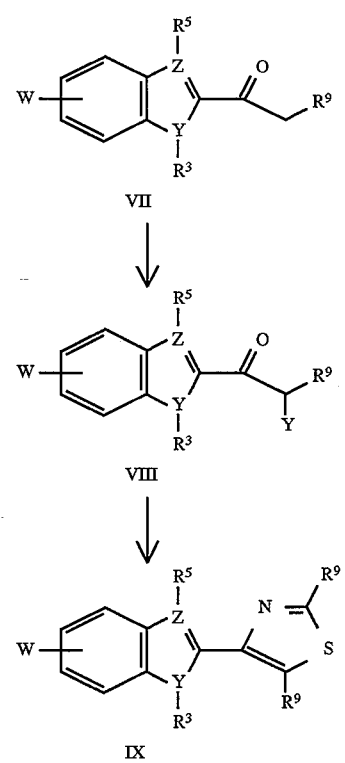
SCHEME 7
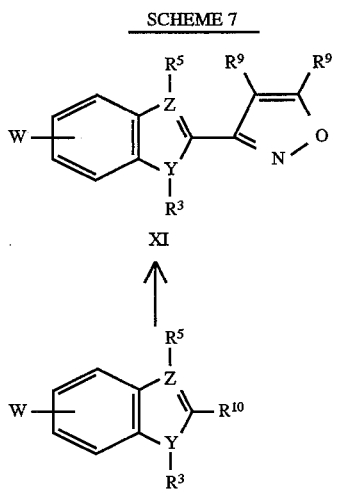

-continued
SCHEME 7

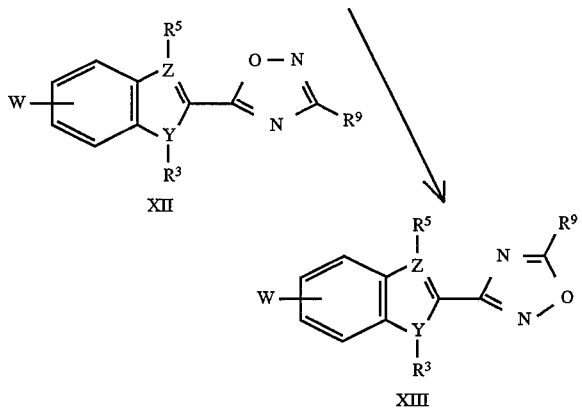

Scheme 1 illustrates the preparation of compounds of the formula I from aldehydes or ketones of formula III.

Referring to Scheme 1, a compound of the formula III is reacted with a compound of the formula IV to produce a compound of the formula I. This reaction is typically carried out in the presence of a reducing agent such as sodium cyanoborohydride, sodium triacetoxyborohydride, sodium borohydride, hydrogen and a metal catalyst, zinc and hydrochloric acid, or borane dimethyl sulfide followed by treatment with formic acid. It is generally conducted at temperatures from about −60° C. to about 50° C. Suitable reaction inert solvents for this reaction include lower alcohols (e.g., methanol, ethanol and isopropanol), acetic acid, chlorinated hydrocarbon solvents (e.g., methylene chloride, chloroform, 1,2 dichloroethane) and tetrahydrofuran (THF). Preferably, the solvent is 1,2-dichloroethane, the temperature is about 25° C., and the reducing agent is sodium triacetoxyborohydride.

Scheme 2 illustrates an alternative method for the preparation of compounds of formula I from amines of formula II.

Referring to Scheme 2, a compound of formula I can be synthesized from compounds of formula II by reaction with an epoxide of the formula V. This reaction is typically carried out by reacting an amine of formula II with an epoxide of formula V in a polar aprotic solvent such as dimethyl sulfoxide, dimethyl formamide, acetonitrile or a lower alkanol such as ethanol, isopropanol or butanol, at a temperature from about −10° C. to about 125° C. Preferably the solvent is dimethyl sulfoxide and the reaction is run at a temperature from about 0° C. to about 10° C.

A preferred modification of the above reaction involves pretreatment of the amine of formula II with N-(trimethylsilyl)-acetamide to form a silyated compound of the formula

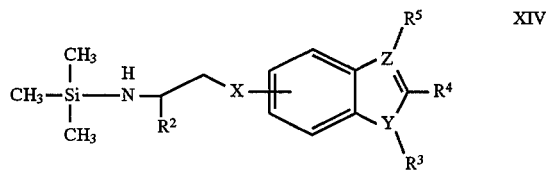

This reaction is typically carried out in a polar aprotic solvent such as dimethyl sulfoxide, dimethyl formamide, acetonitrile or a lower alkanol such as ethanol, isopropanol or butanol, at a temperature from about −10° C. to about 125° C. Preferably, the silyation is carried out at about 25° C. and the reaction with the epoxide is accomplished at about 60° C. After silyation is complete, the compound of formula XIV is reacted with the epoxide of formula V as described above.

Scheme 3 illustrates the preparation of compounds IB and IC from compounds of formula IA. Compounds of formula IA are compounds of formula I wherein $R^4$ is $CO_2R^2$. Compounds of formulae IB and IC are compounds of formula I in which $R^4$ is $CO_2H$ and $CO_2NR^7R^8$, respectfully. Compounds of formula IA are prepared by the methods of Schemes 1 and 2. The transformations depicted in scheme 3 may be accomplished by methods well known to those skilled in the art.

Referring to Scheme 3, compounds of formula IA can be converted into carboxylic acids of formula IB by treatment with an acid or a base. Examples of suitable bases for the reaction are: sodium hydroxide (NaOH), potassium hydroxide (KOH), and lithium hydroxide. Suitable acids for the reaction include: hydrochloric acid (HCl), hydrobromic acid and sulfuric acid. Preferably, the base is potassium hydroxide. The solvent for the aforesaid process is typically a lower alkanol, hexane, DMF, toluene and/or water. The lower alkanol can be methanol, ethanol, propanol or butanol. The reaction temperature may range from about 0° C. to about 100° C. Preferably, the temperature is about 25° C.

Compounds of formula IA can be converted into other esters of the formula IA, in which a different definition of $R^2$ has been substituted, by transesterification. Transesterification is facilitated by reacting a compound of formula IA with acid or base in an excess of an alcohol of the formula $R^2OH$. Suitable acids for the reaction include hydrochloric, hydrobromic, sulfuric and toluene sulfonic acid. Preferably, the acid is hydrochloric acid. The reaction temperature may range from about 0° C. to about 115° C. Suitable solvents include alcohols of formula $R^2OH$, and mixtures thereof with toluene, cyclohexane, DMF and methylene chloride.

Alternatively, compounds of formula IA can be converted into amides of formula IC by treatment of the ester of formula IA with an amine of the formula $R^7R^8NH$. Usually, a polar protic solvent such as a lower alkanol is used, and the reaction is run at a temperature from about 0° C. to about 125° C. for about 0.5 to about 24 hours. Suitable solvents include lower alcohols, and mixtures thereof with toluene, cyclohexane, DMF and methylene chloride. Preferably, the reaction is conducted in methanol at about 65° C. for about 3 to about 24 hours.

Scheme 4 refers to the preparation of compounds of the formulae II and III, wherein X is O or S. Compounds of formulae II and III are the starting materials for the synthesis of compounds of formula I in Schemes 1 through 3. Compounds of formula III, wherein X is O or S, can be used to form compounds of formula I according to the processes of Scheme 1. Compounds of formula II, wherein X is O or S, can be used to form compounds of formula I according to the processes of Scheme 2.

Referring to Scheme 4, compounds of formula II are made by reductive amination of a compound of formula III. The conditions for reductive amination are as described above for the conversion of the ketone of formula III to the compound of formula I in Scheme I, with the exception that the amine used is ammonia or an acid addition salt thereof, instead of the amine of formula IV.

Compounds of formula III can be made in three steps beginning with compounds of the formula XV.

Compounds of the formula XV are first converted to thiols or phenols of the formula XVI by treatment of an ether (when X is O) or a thioether (when X is S) of formula XV with boron tribromide. Suitable solvents for the aforesaid reaction are non-polar aprotic solvents such as methylene chloride, toluene, chloroform, or carbon tetrachloride.

Preferably, the solvent is methylene chloride. The temperature of the reaction may range from about -78° C. to about 20° C. during the reaction with boron tribromide. It is preferably about 0° C.

The thiol or phenol of formula XVI so formed is converted into a ketal or acetal of the formula XVII by treatment with a compound of the formula

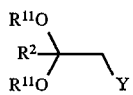

wherein Y is chloro, bromo or iodo, in the presence of a base. Preferably, the thiol or phenol of formula XVI is first converted into an anion by reaction with a base. Examples of appropriate bases include sodium hydride and potassium t-butoxide. The preferred base is sodium hydride (NaH). Examples of suitable solvents for the aforesaid process include polar aprotic solvents such as dimethyl formamide, dimethylsulfoxide, and sulfolane. Preferably, the solvent is dimethyl formamide.

The temperature for the aforesaid reaction ifs in the range of about -10° C. to about 100° C. Preferably, the temperature is 30° C.

The ketal or acetal of formula XVII so formed is converted into the corresponding compound of formula III by reaction with an acid. Typically, this reaction is conducted at a temperature in the range of about 10° C. to about 100° C. Examples of appropriate acids for the aforesaid process are hydrochloric, hydrobromic and sulfuric acids. Preferably, the acid is hydrochloric acid. Suitable solvents for the aforesaid process include polar solvents such as acetone and/or water. Preferably, the solvent is acetone.

Scheme 5 refers to the preparation of compounds of the formulae III and II wherein X is a direct link. Compounds of the formulae III and II are starting materials for the synthesis of the compounds of the invention illustrated in Schemes 1 through 3.

Compounds of formula III, wherein X is a direct link, can be used to form compounds of formula I according to the processes of Scheme 1.

Compounds of the formula II, wherein X is a direct link, can be used to form compounds of the formula I according to the processes of Scheme 2.

Referring to Scheme 5, compounds of the formula III can be converted into compounds of the formula II by reductive amination of a compound of the formula III with ammonia as described in Scheme 1.

Compounds of the formula III are prepared from compounds of the formula VI, by treatment of a compound of the formula VI with a tin reagent of the formula $R^2COCH_2Sn(CH_3CH_2CH_2CH_3)_3$ in the presence of palladium (II) acetate and tri-o-tolylphosphine. The tin reagent, $R^2COCH_2Sn(CH_3CH_2CH_2CH_3)_3$, is formed by reaction of tributyltin methoxide with a compound of the formula

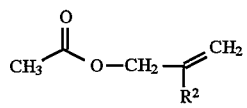

Suitable solvents for the aforesaid process include nonpolar solvents such as toluene, benzene and hexane. Preferably, the solvent is toluene. The temperature for the aforesaid process is generally in the range of about 10° C. to about 150° C., and is preferably about 95° C.

Scheme 6 refers to the preparation of compounds of formula IX, wherein W is bromo, —OCH₃ or —SCH₃.

Compounds of formula IX wherein W is bromo are compounds of formula VI in Scheme 5, wherein $R^4$ is a group of the formula

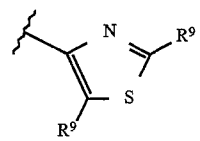

wherein each $R^9$ is selected independently from the other $R^9$ and is selected from the group consisting of hydrogen, $(C_1-C_6)$alkyl optionally substituted with one or more halo atoms, preferably from one to three halo atoms, —$(CH_2)_n$—$NR^7R^8$, —$(CH_2)_n$—$CO_2R^{11}$, halo, nitro, cyano,

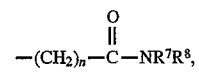

—$(CH_2)_n$—$OR^{11}$, —$(CH_2)_n$—$SO_3R^{11}$, —$(CH_2)_n$—$SO_2$—$(C_1-C_6)$alkyl, and —$(CH_2)_n$—$SO_2NR^7R^8$.

Compounds of formula IX wherein W is —OCH₃ or —SCH₃ are compounds of formula XV in Scheme 4, wherein X is oxygen or sulfur and $R^4$ is a group of the formula

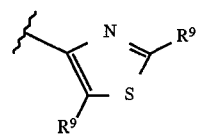

wherein each $R^9$ is selected independently from the other $R^9$ and is defined as above.

Referring to Scheme 6, a compound of formula IX, wherein $R^9$ is defined as above is formed in two steps beginning with a compound of formula VII. The compound of formula VII is reacted with a suitable halogenating agent such as liquid of bromine, N-bromosuccinimide, N-chlorosuccinimide or chlorine gas in the presence of light to form an α-haloketone of the formula VII wherein Y is chloro, bromo or iodo. This reaction is typically carried out in a solvent such as carbon tetrachloride, chloroform or methylene chloride, preferably carbon tetrachloride, at a temperature from about 10° C. to about 100° C., preferably about 30° C.

The α-haloketone of formula VIII is converted into the thiazole of formula IX by reaction of the α-haloketone of formula VIII with a thioamide of the formula

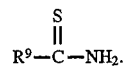

wherein $R^9$ may be a different $R^9$ than the $R^9$ of the α-haloketone and $R^9$ is defined as above.

This reaction is typically carried out in a polar protic solvent such as a lower alkanol, DMF, DMSO, or digylme. Suitable alcohols include methanol, ethanol, propanol and butanol. The reaction temperature may range from about 20° C. to about 150° C. Preferably, the reaction is carried out in ethanol at a temperature of about 80° C.

Scheme 7 refers to the preparation of compounds of the formulae XI, XII and XIII wherein W is bromo, —OCH₃ or —SCH₃. Compounds of the formula XI wherein W is bromo are compounds of formula VI in Scheme 5 wherein $R^4$ is

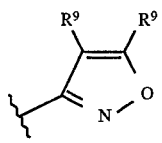

and R⁹ is defined as above and each R⁹ is selected independently from the other R⁹.

Compounds of formula XI wherein W is —OCH₃ or —SCH₃ are compounds of formula XV in Scheme 4 wherein X is oxygen or sulfur and R⁴ is

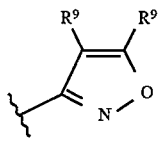

and R⁹ is defined as above and each R⁹ is selected independently from the other R⁹.

Compounds of formula XII wherein W is bromo are compounds of formula VI in Scheme 5 wherein R⁴ is

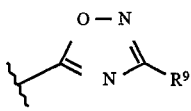

and R⁹ is defined as above.

Compounds of formula XII wherein W is —OCH₃ or —SCH₃ are compounds of formula XV in Scheme 4 wherein X is oxygen or sulfur and R⁴ is

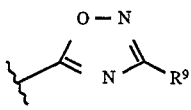

and R⁹ is defined as above.

Compounds of formula XIII wherein W is bromo are compounds of formula VI in Scheme 5 wherein R⁴ is

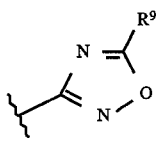

and R⁹ is defined as above.

Compounds of formula XIII wherein W is —OCH₃ or —SCH₃ are compounds of formula XV in Scheme 4 wherein X is oxygen or sulfur and R⁴ is

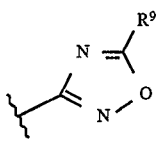

and R⁹ is defined as above.

Referring to Scheme 7, compounds of formula X wherein R¹⁰ is —COCH₂R⁹ and R⁹ and W are defined as above are converted into isoxazoles of formula XI by a two step process. Compounds of formula X are first converted into oximes of the formula

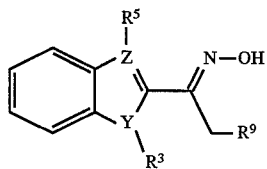

by treatment of the ketone of formula X with hydroxylamine in a polar solvent such as a lower alkanol and/or water. Suitable alcohols include methanol, ethanol and isopropanol. The reaction temperature may range from about 20° C. to about 100° C.

The oxime of formula XVII is converted into the isoxazole of formula XI by reaction with two equivalents of a strong base such as lithium diisopropyl amide, phenyl lithium or N-butyl lithium, followed by addition of an amide of the formula

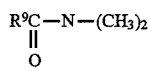

and R⁹ may be a different R⁹ than the R⁹ of the oxime and R⁹ is defined as above, and subsequent cyclization with hydrochloric acid in dioxane at reflux. Modifications of this process are described in G. N. Barber, *Journal of Organic Chemistry*, 43, 3015–3021 (1978).

Scheme 7 also describes the synthesis of 3,5-disubstituted-1,2,4-oxadiazoles of formula XII from compounds of formula X, wherein R¹⁰ is an ester equivalent of formula —COR¹¹, and wherein R¹¹ is halo or alkoxy. The ester of formula X is reacted with an amidoxime of the formula

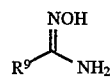

and R⁹ is defined as above, to form the oxadiaxole of formula XII, according to the procedure described in Swain et al., *J. Med. Chem.* 43, 140–151 (1991).

Scheme 7 also describes the synthesis of 3,5 disubstituted 1,2,4-oxadiazoles of formula XIII. Oxadiazoles of formula XIII can be synthesized by reacting compounds of formula X, wherein R¹⁰ is an amidoxime of the formula

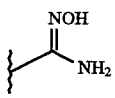

with an ester equivalent (i.e. R⁹COCl) or a compound of the formula R⁹C(OR²)₃, wherein R⁹ is defined as above, according to the procedure of Shine et al., *J. Heterocyclic Chem.*, 26, 125–128 (1989).

The compounds of formula J can be prepared according to the methods described in U.S. Pat. No. 5,061,727, which issued on Oct. 29, 1991.

The compounds of formula K can be prepared according to the methods described in U.S. Pat. No. 4,338,333, which issued on Jul. 6, 1982.

The compounds of formula L can be prepared according to the methods described in European Patent Publication 516,349, published Dec. 2, 1992.

U.S. Pat. Nos. 5,061,727 and 4,338,333 and European patent publication 516,349 are all incorporated herein by reference in their entireties.

The pharmaceutically-acceptable cation salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The amino acid prodrugs of this invention may be prepared by conventional peptide coupling reactions coupling a free amino or carboxylic group of the compound of formula I with an amino acid or a polypeptide, e.g. dipeptide, chain. The coupling reaction is generally conducted at a temperature of about −30° to about 80° C., preferably about 0° to about 25° C. Suitable coupling reagents are usually present, such as dicyclohexylcarbodiimide with hydroxybenzotriazole (HBT), N-3-dimethylaminopropyl-N'-ethylcarbodiimide with HBT, 2-ethoxy-1-ethoxycarbonyl-1,2-dihydroquinoline, carbonyl diimidazole with HBT, or diethylphosphoryl-cyanide. The reaction is generally conducted in an inert solvent such as acetonitrile, methylene chloride, chloroform, dimethylformamide, dioxane, tetrahydrofuran, dimethoxyethane, or water, or a mixture of two or more such solvents.

Ester, carbonate or carbamate prodrugs of this invention may be prepared by reaction of a free hydroxyl or amino group of the compound of formula I with an activated carbonyl containing molecule such as acetyl chloride or ethyl chloroformate. The reaction can be carried out neat or in the presence of a reaction inert solvent such as methylene chloride, at a temperature from about −78° to about 100° C. Alcohols can also be reacted with cyanogen chloride in the presence of a Lewis acid to form carbamates. Ester and amide prodrugs of free carboxylic acid groups can be made according to the methods of scheme 3.

Prodrugs in which the secondary amine and its β hydroxy, taken together, form a group of the formula

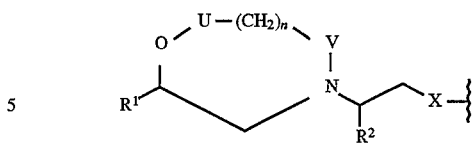

are formed by methods analogous to those described in U.S. Pat. No. 4,593,023 to Beecham issued on Jun. 3, 1986, European Patent Application 170,135A to Beecham published on Jul. 21, 1984 and U.S. Pat. No. 4,607,033 issued on Aug. 19, 1986 to Beecham.

When treating or preventing intestinal motility disorders such as irritable bowel syndrome, peptic ulceration, esophagitis, gastritis and duodenitis, (including that induced by H. pylori), intestinal ulcerations (including inflammatory bowel disease, ulcerative colitis, Crohn's disease and proctitis) and gastrointestinal ulcerations, depression, prostate disease, neurogenetic inflammation and dyslipidemia generally satisfactory results are obtained when the compounds of the formula I, J, K or L and the pharmaceutically acceptable salts thereof are administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.05 to about 50 mg/kg body weight of the subject per day, preferably about 0.1 to about 10 mg/kg body weight per day, administered singly or as a divided dose. However, the optimum dosage for the individual subject being treated will be determined by the person responsible for the treatment, generally smaller doses being administered initially and thereafter increments made to determine the most suitable dosage. This will vary according to the particular compound employed and with the subject being treated.

When treating or preventing intestinal motility disorders, preferable results are obtained when the compounds of the formula I, J, K or L are administered at a daily dosage of from about 1 milligram to about 10 milligrams per kilogram of body weight, preferably given in divided doses 4 times a day, or in sustained release form. For most large mammals, the total daily dosage is from about 10 milligrams to about 1000 milligrams, preferably from about 10 milligrams to about 300 milligrams. In the case of a 70 kg adult human, the total daily dose will generally be from about 10 milligrams to about 300 milligrams. This dosage regimen may be adjusted to provide the individual optimal therapeutic response.

When treating or preventing depression, preferable results are obtained when the compounds of the formula I, J, K or L are administered at a daily dosage of from about 1 milligram to about 10 milligrams per kilogram of animal body weight, preferably given in divided doses 4 times a day, or in sustained release form. For most large mammals, the total daily dosage is from about 10 milligrams to about 1,000 milligrams, preferably from about 10 milligrams to about 300 milligrams. In the case of a 70 kg adult human, the total daily dose will generally be from about 10 milligrams to about 300 milligrams. This dosage regimen may be adjusted to provide the optimal individual therapeutic response.

When treating or preventing prostate disease, preferable results are obtained when the compounds of the formula I, J, K or L are administered at a daily dosage of from about 1 milligrams to about 10 milligrams per kilogram of animal body weight, preferably given in divided doses 4 times a day, or in sustained release form. For most large mammals, the total daily dosage is from about 10 milligrams to about 1000 milligrams, preferably from about 10 milligrams to about 300 milligrams. In the case of a 70 kg adult human, the total daily dose will generally be from about 10 milligrams to about 300 milligrams. This dosage regimen may be adjusted to provide the optimal individual therapeutic response.

When treating or preventing dyslipdemia, preferable results are obtained when the compounds of the formula I, J, K or L are administered at a daily dosage of from about 0.1 milligram to about 10 milligrams per kilogram of animal body weight, preferably given in divided doses 4 times a day, or in sustained release form. For most large mammals, the total daily dosage is from about 1 milligrams to about 1000 milligrams, preferably from about 1 milligrams to about 50 milligrams. In the case of a 70 kg adult human, the total daily dose will generally be from about 1 milligrams to about 50 milligrams. This dosage regimen may be adjusted to provide the individual optimal therapeutic response.

The compounds of the formula I, J, K and L are preferably used in combination with a pharmaceutically acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds of then formula I, J, K or L can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds of formula I, J, K and L may also be administered parenterally. For parenteral administration the compounds I, J, K or L can be combined with sterile aqueous or organic media to form injectable solutions or suspensions. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly, with intramuscular administration being the preferred parenteral route in man.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of micoorganisms such as bacteria and fungi.

The effective dosage of the active ingredient employed may vary depending on the particular compound employed, the mode of administration, the condition being treated and the severity of the condition being treated.

Selectivity of a compound for $\beta_3$-receptors over $\beta_2$ and $\beta_1$ receptors may be determined using the following procedures.

In vitro selectivity may be determined by measurement of cyclic Adenosine mono-phosphate (cAMP) in Chinese hamster ovary cells. Chinese hamster ovary cells uniquely transfected with the gene for the human $\beta_1$, $\beta_2$ or $\beta_3$ receptor are grown to confluence in Ham's F12 media containing 10% fetal bovine serum, 500 µg/ml Geneticin, 100 U/ml penicillin, 100 µg/ml streptomycin and 250 ng/ml Fungizone. Compounds are dissolved in Hams F12 media, and added to the cells at $10^{-10}$–$10^{-5}$M along with $10^{-3}$M isobutylmethylxanthine to inhibit phosphodiesterase activity. The media and cells are then incubated for 10 minutes at 37° C. At the end of this period, the media is aspirated, the cells dissolved in 0.01N hydrochloric acid and then the media is neutralized with 1N sodium hydroxide. The cellular content of cAMP can then be determined by Radioimmuno Assay (RIA) using a kit from New England Nuclear. There is a direct correlation between the cellular content of cAMP and the agonism of the $\beta_3$-receptor.

In vivo efficacy may be determined by measurement of oxygen consumption in male Sprague-Dawley rats. Whole animal oxygen consumption may be measured using an open circuit, indirect calorimeter (Oxymax™, from Columbus Instruments, Columbus, OH). The Oxymax gas sensors are calibrated with nitrogen ($N_2$) gas and gas mixture (0.5% carbon dioxide ($CO_2$), 20.5% oxygen ($O_2$), 79% $N_2$) before each experiment. Rats (male, Sprague Dawley, 300–380 g body weight) are placed in sealed chambers (43×43×10 cm) of the calorimeter and the chambers placed in activity monitors. Air flow rate through the chambers is set at 1.6–1.7 l/min. The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis; ambulatory activity is recorded when two consecutive beams are broken (repeated interruptions of the same beam are not registered) and the results are recorded as counts. Basal oxygen consumption and ambulatory activity can be measured every 10 minutes for 2.5 to 3 hours. At the end of the basal period, the chambers are opened and the test compound (0.01 to 10 mg/kg, prepared in saline) or an equivalent volume of saline is administered by oral gavage. Oxygen consumption and ambulatory activity can be measured every 10 minutes for an additional three hours post-dosing. Percent change in oxygen consumption may be calculated by averaging the post-dosing values for 2.5 hours and dividing by basal oxygen consumption (average of the predosing values except the first hour). Oxygen consumption values obtained during time periods where ambulatory activity exceeded 100 counts are excluded from the calculation. Thus, the values represent % change in resting oxygen consumption.

In vivo selectivity for $\beta_1$ and $\beta_2$ adrenoceptors may be determined by measurements of heart rate and blood pressure gathered on rats (male, Sprague Dawley, 300–380 g body weight) anesthetized with pentobarbital (50–60 mg/kg, i.p.). The left carotid artery is cannulated with PE50 tubing. The catheter is tunneled subcutaneously, exteriorized at the back of the neck, filled with a solution of polyvinylpyrrolidone in heparinized saline, flame-sealed and taped. Experiments are performed 7 days after surgery. On the day of the experiment, the catheters are untaped and flushed with saline. After at least 30 minutes, basal values for heart rate and blood pressure were measured by attaching the catheter to a pressure transducer and the results recorded on a Grass Model 7 polygraph. After obtaining basal values, the test compound or vehicle is administered by oral gavage, and blood pressure (measure of $\beta_2$ activity) and heart rate (measure of $\beta_1$ activity) measurements are taken at 15, 30, 45 and 60 minutes. To determine changes, basal values are subtracted from the average of the post dosing values.

All of the compounds of the invention were tested in the in vitro model and showed better than a four fold increase in cAMP levels at a dose of 10 µM.

Compounds of the formula I, J, K or L also have the effect of reducing intestinal motility and thus find utility as aiding in the treatment of various gastrointestinal disorders such as irritable bowel syndrome, peptic ulceration, esophagitis, gastritis and duodenitis, (including that induced by *H. pylori*), intestinal ulcerations (including inflammatory bowel disease, ulcerative colitis, Crohn's disease and proctitis) and gastrointestinal ulcerations. It has been proposed that the motility of non-sphincteric smooth muscle contraction is mediated by activity as $\beta_3$ adrenoreceptors. The availability of a $\beta_3$ specific agonist, with little activity at $\beta_1$ and $B_2$ receptors will assist in the pharmacologic control of intestinal motility without concurrent cardiovascular effects.

In vivo activity of the compounds of formula I for the treatment or prevention of intestinal motility disorders can be determined according to the following procedures. Eighteen-hour fasted male Sprague Dawley derived (CD) rats (175–225 grams) are dosed with 0.1, 1.0, or 2.0 mg/kg p.o. of compound or vehicle (distilled water). Thirty minutes after drug administration, the rats are orally dosed with 0.25 ml of a solution of sodium chromate in 0.9% saline containing about 20,000 cpm of $^{51}Cr$ (specific activity 350 mCi/mg Cr). Twenty minutes later, the rats are sacrificed, the gastroesophageal, pyloric, and ileocecal junctions are then ligated, and the stomachs and small intestines removed. The small intestines are then divided into ten equal lengths, and the stomach and each length of intestine assayed for radioactivity with a gamma counter. Gastric emptying rate may then be determined for each rat by comparing the amount of radioactivity in the intestine relative to the total in the intestine plus stomach. In addition, the geometric center of the distribution of the radioactive marker is then used as a measure of the overall transit rate through the stomach and intestine. The geometric center is calculated by summing the products of the fractions of $^{51}Cr$ in each segment times the segment number: geometric center=$\Sigma$ ((fraction of $^{51}Cr$ per segment)×(segment number)). For these calculations the stomach may be considered segment number 0, and the ten intestinal segments as numbers 1 to 10. Thus, a geometric center of 0.0 would indicate that the entire load of $^{51}Cr$ had remained in the stomach. Data from two experiments may be pooled, and statistical evaluations were made using Dunnett's multiple comparison test.

Alternatively, in groups of 8, overnight-fasted male Sprague-Dawley (CD) rats (175–225 grams) may be anesthetized with methoxyflurane. A small abdominal incision is then made, and the pylorus can then be ligated. Immediately after the ligation, a solution of compound or the vehicle (distilled water) is injected into the proximal duodenum. The doses of drug used should be 0.1, 1.0 and 2.0 mg/kg. The incisions can then be closed and the rats can be allowed to recover from the anesthesia. Two hours after the ligation the rats are sacrificed and the gastric fluid collected and cleared by centrifugation. Total volume of secretion can be determined by weight, and acidity can be determined by titration to pH 7.0 with 0.1N NaOH using an automatic titrator (Radiometer TTT85). The data from two experiments is then pooled. A group of rats treated with 10 mg/kg of the antisecretory histamine $H_2$-receptor antagonist cimetidine may be included in each experiment as a positive control. Statistical evaluations can be made using Student's t-test.

In vitro activity for relaxation of contracted ileum from isolated guinea pig ileum can be determined according to the following procedure. Fresh isolated segments of guinea pig ileum (about 1.5 cm long) are mounted in tissue baths containing Tyrode's physiological salt solution at 30° C. and aerated continuously with $O_2:CO_2$ (95%:5%). Tissues are then equilibrated for 60–90 minutes under 4.0 gm tension in order to achieve stable baselines. Histamine is then added to the baths in a cumulative fashion in concentrations ranging from 1 nM to 10 µM. The maximum tension generated after each addition of histamine is recorded on a Grass Physiograph. The tissues are then washed with several changes of Tyrode's solution, basal tension can be readjusted to 4.0 grams, and a stable baseline is then again obtained. Each tissue may then be exposed to a single concentration of test compound (range 1 nM to 10 µM) or vehicle and after a 30 minute equilibration period, the histamine does response curve may then be repeated. Results from multiple experiments are standardized (0–100%) to the maximum response of the control tissues and plotted as percent maximum tension versus the log of the histamine concentration in the absence and presence of the drug.

In vivo activity of the compounds of formula I, J, K or L for depression can be determined according to the following procedures.

Male CD-1 mice (25–30 g, fasted overnight) are be randomly assigned to treatment groups and given vehicle or test compound at doses of 32, 10, 3.2, 1.0, 0.32, 0.1, or 0.032 mg/kg. The compound of formula I (in 5% Emulphor: 5% ethanol: 90% saline) is administered by oral gavage. Isoproterenol, which should be used as a control standard, has poor bioavailability and, for this reason, can be administered in saline vehicle by the subcutaneous route. Evaluations should be conducted "blind" with changes in overt behavior assessed one half hour, one hour and two hours after drug administration using a modification of the quantitive scoring system described by Irwin S., *Drug Screening and Evaluation of New Compounds in Animals*. n: Nodine J. H. Siegler P. E. eds. Pharmacologic Techniques in Drug Evaluation. Chicago: Yearbook Medical Publishers, (1964). Briefly, animals should be placed in Plexiglas® cubicles (dimensions: 15×15×18 cm) and observations made of undisturbed behavior. Mice may then be transferred to a large observation box and evaluated individually for changes in locomotor activity, reflexes, muscle tone and autonomic nervous system function. Seven behaviors (e.g.

convulsions, death, urination/defecation) are scored as present or absent and their frequencies expressed as the percent of animals exhibiting the response. Sixteen other behaviors, such as piloerection, disturbance of gait, ptosis, positional passivity, body position, locomotion, respiration rate, transfer arousal, body/abdominal tone, limb tone, provoked biting, tail pinch, toe pinch, corneal reflex, skin color, inverted screen, pupil size (30× mm), may be scored using a 0–8 scale, with values of 0, 2, 4, 6 and 8 representing none, slight, moderate, marked and extreme magnitudes of behavior, respectively. Scores for normal behavior in drug-naive animals may be reported either as 0 (e.g. for disturbance of gait, positional passivity) or 4 (e.g. for body position, locomotion respiration rate and transfer arousal). An inverted screen (scored on a 0–2 scale) may be used to assess motor coordination and grip strength. Pupil sizes can be measured using the reticle of a binocular microscope. Following the initial 2 hr observation period, animals may be retained for 24 hr to determine the incidence of delayed mortality.

Alternatively, compounds of formula I can be assessed for antidepressant activity according to the following procedure.

Male CD1 mice weighing between 20 and 25 g, and Sprague-Dawley rats weighing between 200 and 250 g, may be obtained from Charles River, USA. Hydrochloride salts of compounds of formula I are dissolved in water. The compounds may be administered to mice in a volume of 10 ml $kg^{-1}$, and to rats in a volume 2 ml $kg^{-1}$. Control animals receive the vehicle. Positive test results for the following nine parameters indicate antidepressant activity.

I. Effect on basal rectal temperature:

Mice are given drug or its vehicle, and their rectal temperatures recorded 30, 60, 90, 120 and 180 min later by means of a thermometer and a thermoelectric probe inserted at a constant depth into the rectum.

II. Antagonism of hypothermia induced by reserpine:

Mice are given reserpine (2.5 mg $kg^{-1}$ i.p. dissolved in 1% citric acid). Their rectal temperatures may be measured 3.5 h later. The mice may then be divided into different groups so as to obtain the same mean rectal temperature in each group. Half an hour later (i.e. 4 h after reserpine), the mice are given the vehicle or test drug. Rectal temperature can be measured again 90 min later (i.e. 5 h 30 after the injection of reserpine) (Bourin et al., *The Value of the Reserpine Test in Psychopharmacology*, Arzneim. Forsch. 33, 1173, (1983)).

III. Antagonism of hypothermia induced by apomorphine:

Half an hour after the mice are placed in individual cages, their rectal temperatures are recorded. The animals should be allocated so as to obtain the same mean rectal temperature in each group. Apomorphine (16 mg $kg^{-1}$ s.c.) can be given 30 min after the test drug or its vehicle. Rectal temperature can be measured again 30 min after the apomorphine treatment (Puech et al, *Antagonism of Hypothermia And Behavioural Response To Apomorphine; A Simple, Rapid And Discriminating Test For Screening Antidepressants And Neuroleptics*, Psychopharmacology 75, 84, (1981)).

IV. Potentiation of lethality induced by yohimbine:

This test can be performed on groups of 10–20 mice basically as described by Quinton, R. M., *The Increase In The Toxicity Of Yohimbine Induced By Imipramine And Other Drugs In Mice*, Br. J. Pharmacol. 21, 51 (1963). Test drugs or vehicle can be administered i.p. 30 min before the adminsitration of yohimbine. Yohimbine hydrochloride can then be administered s.c. at a does of 30 mg $kg^{-1}$ (expressed in terms of the salt) always at the same time of day, between 1.30 and 3.30p.m. Lethality can be recorded the next morning at 9a.m.

V. Antagonism of ptosis induced by reserpine:

Mice are given the vehicle or drug, and 60 min later injected with reserpine (2 mg $kg^{-1}$ i.v., dissolved in dilute ascorbic acid) (Gouret et al., *Interaction De Divers Psychotropes Avee Cinq Effects de la Reserpine Chez la Souris Et Chez Le Rat; Ptose Palpébrale, Hypothermine, Hypomotilité, Catalepsie Et Pointes Pontogéniculo-Occipitales*. J. Pharmacol. (Paris) 8, 333,(1977)). One hour later, the degree of ptosis in each eye can be measured in each mouse as 0 (eye completely open) to 4 (eye full closed). This gives a maximum score of 8 per mouse.

VI. Activity in the behavioral despair test in mice:

Sixty minutes after the administration of the test drug or its vehicle, the mice are individually forced to swim in an open cylindrical container (diameter 10 cm, height 25 cm), containing 8.5 of water at 22°±1° C.; the total duration of immobility during the last 4 min of a single 6-min test session can be scored. A mouse should be considered to be immobile whenever it remained floating in the water in a slightly hunched position, its head just above the surface (Porsolt et al., *Pharmacological models of Depression*. In: Animal Models in Psychopharmacology. Advances in Pharmacological Science, eds. B. Olivier, J. Mos and J. L. Slangen (Birkhauser Verlag, Berlin) p. 137, 1977).

VII. Effect of learned helplessness behavior:

This test is performed basically as described by Giral el al. *Reversal Of Helpness Behaviour In Rats By Putative 5-$HT_{IA}$ Agonists*. Biol. Psychiat. 23, 237. (1988). Electric foot-shocks are delviered to male albino Sprague-Dawley rats placed in chambers (20×10×10 cm) with plexiglass walls and covers. The floors are made of stainless-steel grids (1.5 cm mesh). A constant-current shocker is delivered at 60 scrambled, randomized inescapable shocks (15 s duration, 0.8 mA, every 60+15 s) to the grid floor. Control rats are then placed in identical chambers for 1 h but no shock is administered. All preconditioning trials are performed on day 1 between 9 and 11a.m. Avoidance training is initiated 48 h (day 3) after inescapable shock in automated two-way shuttle-boxes (60×21×30 cm) with plexiglass walls and a floor consisting of stainless-steel rods spaced 1.0 cm apart in order to evaluate escape deflicts. Each shuttle-box is divided into two chambers of equal size by a stainless-steel partition, with a gate providing access to the adjacent compartment through a 7×7 cm space. Shuttle-box sessions are performed for 3 consecutive days (days 3, 4 and 5). The animals are placed individually in the shuttle-box and allowed to habituate to the environment for 5 min (for the first session only) and then subjected to 30 trials. The intertrial interval should be 30 s. A light signal, used as a conditioned stimulus, is presented during the first 3 s of each trial. Crossing the gate into the other compartment of the box during this 'conditioned-stimulus only' period (referred to as avoidance response) allows the rats to avoid shocks. A period with conditioned stimulus plus electric foot-shock (0.8 mA) may be presented if an avoidance response does not occur. Crossing the gate into the other compartment during this conditioned stimulus plus shock period is referred to as an escape response. Absence of escape response during the 3-s duration conditioned stimulus plus shock should be considered to be an escape failure.

The rats (n=10 per group) should be treated randomly according to one of the following protocols: the control sample, which receives no shock, and is given vehicle; experimental animals with inescapable shock are treated daily with vehicle or drug. Animals should be treated orally over 5 consecutive days, i.e. 6 h after shock pretreatment on day 1, and then twice per day, a half dose in the morning (30 min before shuttle-box session) and a half dose in the afternoon (except on the 5th day). Statistical analysis can be performed on the mean number of escape failures using a two-way analysis of variance (subjects X sessions) followed by Dunnett's test.

VIII. Effect on locomotor activity

Locomotor activity of mice is measured by means of photocells in a series of activity cages (Apelex, France), linked to a control unit and printer. The animals are placed singly in activity cages 30 min after treatment and motility was assessed over a period of 30 min (Boissier, J. R. and P. Simon *Action De La Caféine Sur La Motilité Spontanéé De La Souris, Arch. Int. Pharmacodyn*, 158, 212. (1965)).

IX. Evaluation of drug-induced drinking

For the determination of drug-induced drinking, rats are placed in individual cages fitted with special water dispensers. The dispensers allow the animal free access to the water bottle nozzle. Vehicle or drug is administered and the water intake may be measured after 3 hours by weighing the water bottle. The volume of fluid drunk may be calculated by subtraction, assuming the density of water to be 1.0 g/ml. The animals must be allowed at least 24 h to become accustomed to the novel environment of the individual cage before the experiment is performed (Lehr et al., *Copious Drinking And Simultaneous Inhibition Of Urine Flow Elicited By Beta-Adrenergic Stimulation And Contrary Effect of Alpha-Adrenergic Stimulation*. J. Pharmacol. Exp. Ther. 158, 150. (1967)).

In vivo activity of the compounds of formula I, J, K or L for prostate disease can be determined according to the following procedure.

Male rabbits (CEGAN) weighing 3 to 4 kg are sacrificed by exsanguination and cervical dislocation.

The bladder and urethra are rapidly removed and placed in lukewarm Krebs solution containing bicarbonate.

The composition of this Krebs medium is as follows, in mM: sodium chloride (NaCl) 114 potassium chloride; (KCl) 4.7; calcium chloride ($CaCl_2$) 2.5; potassium dihydrogen phosphate ($KH_2PO_4$) 1.2. magnesium sulfate ($MgSO_4$) 1.2; sodium bicarbonate ($NaHCO_3$) 25.0; glucose 11.7; ascorbic acid 1.1. Propranolol (1.0 μM) is added into the Krebs medium to block the β-adrenergic receptors.

The bladder is opened transversely and the "trigone" region of the muscle, located on the dorsal surface of the bladder and between the two ureters, is dissected out.

A 5 mm ring of urethra, from the region situated between the base of the bladder and the prostate, is also prepared.

The portions of trigone muscle and urethra are washed under a tension of 1 g in Krebs medium.

The contraction-response curve to cumulated concentrations of phenylephrine is determined.

Additions of the agonist are performed every 5 min. The tissues are washed until the original tension is reestablished, and are then incubated for 30 min. with the active agent. A second response curve to the phenylephrine is determined in the presence of the active agent.

The response curves to concentrations of phenylephrine in the presence or absence of drug are expressed as a percentage of the maximum response obtained relative to the control curve.

By means of clinical studies, it can also be possible to show the efficacy of active agents in patients suffering from dysuria of neurological origin with urethral hypertonia.

Five milligrams of drug is injected intravenously continuously for a period of 20 min. Sphincterometric measurements are made using an electronic micro-sensor, before and after the injection of the drug, at the bladder neck and at the striated sphincter of the posterior urethra.

Compounds of the formula I, J or L lower triglyceride levels and cholesterol levels and raise high density lipoprotein levels and are therefore of use in combating medical conditions wherein such lowering (and raising) is thought to be beneficial. Thus they may be used in the treatment of hypertriglyceridaemia, hypercholesterolemia and conditions of low HDL (high density lipoprotein) levels in addition to the treatment of atherosclerotic disease such as of coronary, cerebrovascular and peripheral arteries, cardiovascular disease and related conditions.

The active compounds may also be combined with other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA;cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; and thyromimetics.

Activity of compounds of formula I, J or L for dysilpidemia can be determined according to the following procedure. C57BL/6J ob/ob mice (male, 30–40 g body weight, Jackson Lab, Bar Harbor, Me.), housed 5 mice per cage in an enviromentally controlled room, can be dosed once daily for 3 weeks with drug (0.1, 1 or 3 mg/kg, n=15 per group) or vehicle (saline) by oral gavage. Body weight of each mouse can be measured daily and food intake per cage was determined by weighing the amount of food left in the trough. At the end of the study, 24 h after giving the final dose of compound, the mice may be killed by decapitation and blood collected. Plasma concentrations of glucose, free fatty acids and triglyceride can be determined with the VP Super System Autoanalyzer (Abbot, Irving, Tex.).

Compounds of the formula I, J, K or L inhibit the release of neuropeptides in certain sensory fibara in the lung. As sensory nerves may play an important role in the neurogenic inflammation of airways, including cough, the instant specific β$_3$ agonists may be useful in the treatment of neurogenetic inflammation, such as asthma, with minimal effects on the cardiopulmonary system.

The present invention is illustrated by the following Examples. However, it should be understood that the invention is not limited to the specific details of these examples.

EXAMPLES

Procedure A

Methyl 5-hydroxybenzofuran-2-carboxylic acid

To a stirred solution of ethyl 5-methoxybenzofuran-2-carboxylic acid (5.0 g, 26 mmol) in dichloromethane ($CH_2Cl_2$) (100 ml) at 0° C. was added boron tribromide (8.6 mL, 91 mmol) and the resulting dark solution was allowed to stir at room temperature for 2 hours. The reaction solution was poured over ice, stirred for 30 minutes and extracted with ethyl acetate (EtOAc). The organic phase was washed with water, saturated aqueous brine, dried over sodium sulfate, ($Na_2SO_4$), and concentrated in vacuo to afford 5-hydroxybenzofuran-2-carboxylic acid (4.0 g; m.p. 223°–228° C.).

Compounds of the formula I, J, K or L inhibit the release of neuropeptides in certain sensory fibara in the lung. As sensory nerves may play an important role in the neurogenic inflammation of airways, including cough, the instant specific β₃agonists may be useful in the treatment of neurogenetic inflammation, such as asthma, with minimal effects on the cardiopulmonary system.

Gaseous hydrochloric acid was bubbled into a cooled (0° C.), stirred solution of the above acid in methanol (50 mL) over a 15-min period. The resulting solution was then refluxed for 2.5 hours, and was then cooled and concentrated in vacuo. The residue was dissolved in ethyl acetate, washed with water, brine, dried (Na$_2$SO$_4$) and concentrated in vacuo. The resulting solids were flash chromatographed on silica gel (40% ethyl acetate:hexanes) to afford the title compound as a yellow solid, (3.3 g; m.p. 164°–166° C. Analytical calculated for C$_{10}$H$_8$O$_4$: C,62.52H, 4.20. Found C,62.47H, 4.09).

Procedure B

Methyl 5-(2,2-dimethoxyethyloxy)benzofuran-2-carboxylic acid

To a stirred slurry of sodium hydride (0.11 g of 60% in oil, 2.7 mmol) in p-dioxane (10 mL) was added methyl 5-hydroxybenzofuran-2-carboxylic acid (0.5 g, 2.6 mmol) and the resulting green slurry was stirred at room temperature for 15 min. To this slurry was added a solution of bromoacetaldehyde dimethyl acetal (0.5 g, 3.0 mmol) in dimethylformamide (DMF) (10 mL) and the resulting solution was heated at reflux for 15 hours. The reaction mixture was poured into ethyl acetate, washed with water, brine, the organic phased dried (Na$_2$SO$_4$) and concentrated in vacuo. The resulting oil was flash chromatographed on silica gel (25% ethyl acetate:hexanes) to afford the title compound as a colorless solid, (0.16 g; m.p. 74°–74° C.).

Procedure C

Methyl 5-(ethanal-2-oxy)benzofuran-2-carboxylic acid

A solution of methyl 5-(2,2-dimethoxyethyloxy)benzofuran-2-carboxylic acid (0.16 g, 0.6 mmol) in acetone (4 mL) and 2 N aqueous hydrochloric acid (0.3 mL) was refluxed for 3.5 hours. The reaction solution was concentrated in vacuo, dissolved in ethyl acetate, washed with water, brine, dried (Na$_2$SO$_4$) and concentrated in vacuo to afford the title compound as a colorless solid, (0.14 g; m.p. 112°–115° C.).

Procedure D

Methyl 5-(propan-2-one-yl)benzofuran-2-carboxylic acid

A solution of methyl 5-bromobenzofuran-2-carboxylic acid (2.4 g, 9.3 mmol), tributyltin methoxide (4.0 mL, 14 mmol), isopropenyl acetate (1.4 mL, 14 mmol), palladium (II) acetate (0.1 g, 0.5 mmol) and tri-o-tolylphosphine (0.3 g, 1 mmol) in toluene (6 mL) were heated at 95° C. for 2 hours. The reaction solution was concentrated in vacuo and subjected to flash chromatography on silica gel (25% ethyl acetate:hexanes) to afford the title compound as a colorless solid, (1.8 g; m.p. 77°–79° C., Analytical calculated for C$_{13}$H$_{12}$O$_4$: C, 67.25; H, 5.21. Found: C, 67.12; H, 4.95).

Procedure E

5-Methoxy-2-(2-methyl-thiazole-4-yl)-benzofuran

A solution of 2-bromo-1-(5-methoxy-benzofuran-2-yl)-ethanone (0.6 g, 2.2 mmol) and thioacetamide (0.4 g, 5.1 mmol) in ethanol (15 mL) were refluxed for 1 hour. The reaction mixture was concentrated in vacuo and subjected to flash chromatography on silica gel (14% ethyl acetate:hexanes) to afford the title compound as a solid, (0.47 g; m.p. 136°–137° C.).

Example 1

Methyl 5-(2-(2-(S)-hydroxy-3-phenoxy-propylamino)ethoxy)-benzofuran-2-carboxylic acid To a solution of methyl 5-(ethanal-2-oxy)benzofuran-2-carboxylic acid (0.13 g, 0.56 mmol) and 1-amino-3-phenoxypropan-2(S)-ol (0.10 g, 0.61 mmol) in dichloroethane (3 mL) was added glacial acetic acid (0.05 mL) and sodium triacetoxyborohydride (0.18 g, 0.83 mmol) . After 2 hours, the reaction mixture was diluted into ethyl acetate, washed with saturated sodium bicarbonate, brine, the organic layer was dried (Na$_2$SO$_4$) and concentrated in vacuo. The resulting oil was subjected to flash chromatography (silica gel, 5% methanol: chloroform) to afford the title compound as an off-white solid. (0.10 g; m.p. 115°–119° C., Analytical calculated for C$_{21}$H$_{23}$NO$_6$·0.25H$_2$O: C, 64.70; H, 6.08; N, 3.59. Found: C, 64.89; H, 6.15; N, 3.51).

Example 2

Methyl 5-(2(R)-(2-(2-trifluoromethyl-thiazol-4-yl)-2(R)-hydroxyethyl-amino)propyl)-benzofuran-2-carboxylic acid A solution of (R)-(2-trifluoromethyl-thiazol-4-yl)-ethylene oxide (0.20 g, 1.03 mmol) and methyl 5-(2(R)-2-aminopropyl)-benzofuran-2-carboxylic acid (0.20 g, 0.86 mmol) in isopropyl alcohol (1 ml) was refluxed for 1.5 hours. After cooling, the reaction solution was concentrated in vacuo and the resulting oil was flash chromatographed (silica gel, 2% methanol:chloroform) to afford the title compound as an off-white solid (0.09 g); m.p. 99°–100° C.

Example 3

5-(2-(2(S)-Hydroxy-3-phenoxy-propylamino)ethoxy)-benzofuran-2-carboxyliacid

To a stirred solution of methyl 5-(2-(2(S)-hydroxy-3-phenoxy-propylamino)ethoxy)-benzofuran-2-carboxylic acid (0.10 g, 0.25 mmol) in methanol (5 mL) was added a solution of potassium hydroxide (42 mg, 0.75 mmol) in water (0.4 mL). After 15 hours, the reaction solution was concentrated in vacuo, the residue redissolved in water (4 mL) and the pH adjusted to between 5.0 and 5.5. The resulting solids were collected washed with water, diethyl ether and dried in vacuo to afford the title compound as an off-white solid. (78 mg; m.p. 128°–133° C. Analytical calculated for C$_{20}$H$_{21}$NO$_6$·1.25H$_2$O: C, 60.99; H, 6.02; N, 3.56. Found: C, 60.75; H, 5.86; N, 3.30).

Example 4

5-(2-(2(S)-Hydroxy-3-phenoxy-propylamino)ethoxy)-benzofuran-2-carboxylic acid, (2-methoxy-ethyl)-amide A solution of methyl 5-(2-(2(S)-hydroxy-3-phenoxy-propyl-amino)ethoxy)benzofuran-2-carboxylic acid (0.10 g, 0.26 mmol) and 2-methoxyethyl-amine (0.6 mL) in methanol (3 mL) were maintained at reflux temperature for 18 h. The reaction solution was concentrated in vacuo and flash chromatographed on silica gel (5% methanol:chloroform) to afford the title compound as a colorless solid. (92 mg; m.p. 95°–96° C. Analytical calculated for $C_{23}H_{28}N_2O_6 \cdot 0.25H_2O$: C, 63.79; H, 6.63; N, 6.47. Found: C, 63.59; H, 6.39; N, 6.34.)

Example 5

Isopropyl 5-(2-(2(S)-hydroxy-3-phenoxy-propylamino)ethoxy)-benzofuran-2-carboxylic acid Gaseous hydrogen chloride was slowly bubbled into a cooled (0° C.), stirred solution of methyl 5-(2-(2(S)-hydroxy-3-phenoxy-propylamino)ethoxy)-benzofuran-2-carboxylic acid (0.1 g, 0.25 mmol) in 2-propanol (5 ml) over a 5 minute period. The resulting solution was then refluxed for 16 hours, cooled and flash chromatographed (silica gel, 5% methanol:chloroform) to afford the title compound as a colorless solid. (0.09 g; m.p. 105°–106° C. Analytical calculated for $C_{23}H_{27}NO_6$: C, 66.09; H, 6.63; N, 3.35. Found: C, 66.04; H, 6.38; N, 3.31.)

Example 6

2-Bromo-1-(5-methoxy-benzofuran-2-yl)ethanone

To a cooled (0° C.), stirred solution of 5-methoxy-benzofuran-2-oyl chloride (prepared by treatment of 5-methoxy-benzofuran-2-carboxylic acid in refluxing thionyl chloride)(4.6 g, 22 mmol) in diethyl ether (20 ml) and dichloromethane (5 ml) was added a solution of diazomethane (66 mmol) in diethyl ether (45 ml). After 15 minutes gaseous hydrogen bromide was slowly bubbled in over a 20 minute period. After an additional 30 minutes, the reaction mixture was diluted with ethyl acetate, washed with saturated aqueous brine, the organic layer dried over magnesium sulfate ($MgSO_4$) and concentrated in vacuo. The resultant red oil was flash chromatographed (silica gel, 10% ethyl acetate:hexanes) to afford the title compound as a light-yellow colored solid. 2.8 g.

M.p. 86°–87° C.

Example 7

Methyl 5-(2-(2(S)-hydroxy-3-(2-chlorophenoxy)-propylamino)ethoxy)-benzofuran-2-carboxylic acid The title compound was prepared by a procedure similar to that described in Example 1.

M.p. 126°–126.5° C.

Analytical calculated for $C_{21}H_{22}ClNO_6$: C, 60.07; H, 5.28; N, 3.34. Found: C, 59.89; H, 5.22 N, 3.25.

Example 8

Methyl 6-(2-(2(S)-hydroxy-3-phenoxy-propylamino)ethoxy)-benzofuran-2-carboxylic acid The title compound was prepared by a procedure similar to that described in Example 1.

M.p. 110°–111° C.

Analytical calculated for $C_{21}H_{23}NO_6$: C, 65.36; H, 5.86; N, 3.94. Found: C, 65.44; H, 6.02; N, 3.63.

Example 9

6(2-(2(S)-Hydroxy-3-phenoxy-propylamino)ethoxy)-benzofuran-2-carboxylic acid

The title compound was prepared by a procedure similar to that described in Example 1.

M.p. 214°–217° C.

Analytical calculated for $C_{20}H_{21}NO_6 \cdot 0.25H_2O$: C, 63.90; H, 5.76;N, 3.72. Found: C,63.53; H, 5.66; N,3.61.

Example 10

Methyl 5(2-(2-(2-(3-chloro-phenyl)-2(R)-hydroxy-ethylamino)-ethoxy)-benxofuran-2-carboxylic acid The title compound was prepared by a procedure similar to that described in Example 1.

M.p. 104°–106° C.

Analytical calculated for $C_{20}H_{20}ClNO_5$: C, 61.62; H, 5.17; N, 3.59. Found: C, 61.44; H, 4.96; N, 3.56.

Example 11

5-(2-(2-(3-Chloro-phenyl)-2(R)-hydroxy-ethylamino)-ethoxy)-benzofuran-2-carboxylic acid The title compound was prepared by a procedure similar to that described in Example 1.

M.p. 145°–153° C.

Example 12

Methyl 6-(2-(2-(3-chloro-phenyl)-2(R)-hydroxy-ethylamino)-ethoxy)-benzofuran-2-carboxylic acid The title compound was prepared by a procedure similar to that described in Example 1.

M.p. 102°–103° C.

Analytical calculated for $C_{20}H_{20}ClNO_5 \cdot 0.17H_2O$: C,61.14; H, 5.22; N, 3.56. Found: C, 61.02; H, 5.39; N, 3.31.

Example 13

Methyl 5-(2-(2-(2-trifluoromethyl-thiazol-4-yl)-2(R)-hydroxy-ethylamino)-ethoxy)-benzofuran-2-carboxylic acid The title compound was prepared by a procedure similar to that described in Example 1.

M.p. 128°–131° C.

Analytical calculated for $C_{18}H_{17}F_3N_2O_5S$: C, 50.24; H, 3.98; N, 6.51. Found: C, 50.06; H, 3.87; N, 6.28.

Example 14

5-(2-(2-(2-Trifluoromethyl-thiazol-4-yl)-2(R)-hydroxy-ethylamino)-ethoxy)-benzofuran-2-carboxylic acid The title compound was prepared by a procedure similar to that described in Example 3.

M.p. 155°–163° C. Analytical calculated for $C_{17}H_{15}F_3N_2O_5S \cdot 2.25H_2O$: C,44.70; H, 4.30; N, 6.13. Found: C, 44.45; H, 4.30; N, 6.13.

Example 15

1-(5-(2(2(S)-Hydroxy-3-phenoxy-propylamino)-ethoxy)-benzofuran-2-yl)-ethanone

The title compound was prepared by a procedure similar to that described in Example 1.

M.p. 122°–123° C.

Analytical calculated for $C_{21}H_{23}NO_5 \cdot 0.2H_2O$: C, 67.62; H, 6.32; N, 3.75. Found: C, 67.83; H, 6.10; N, 3.73.

Example 16

1-(5-(2(2(S)-Hydroxy-3-phenoxy-propylamino)-ethoxy)-benzofuran-2-yl)-butanone

The title compound was prepared by a procedure similar to that described in Example 1.

M.p. 99°–100° C. Analytical calculated for $C_{23}H_{27}NO_5.0.14H_2O$: C, 69.05; H, 6.87; N, 3.50. Found: C, 69.08; H, 6.76; N, 3.34.

Example 17

1-(2-(2-isoxazol-3-yl-benzofuran-5-yloxy)-ethylamino)-3-phenoxy-propan-2(S)-ol

The title compound was prepared by a procedure similar to that described in Example 1.

M.p. 107°–110° C. Analytical calculated for $C_{22}H_{22}N_2O_5$: C, 66.99; H, 5.62; N, 7.10. Found: C, 66.94; H, 5.42; N, 7.00.

Example 18

1-(2-(2-Isoxazol-3-yl-benzofuran-5-yloxy)-ethylamino)-3-(2-chloro-phenoxy)-propan-2(S)-ol The title compound was prepared by a procedure similar to that described in Example 1.

M.p. 93°–96° C.

Analytical calculated for $C_{22}H_{21}ClN_2O_5 \cdot 0.25H_2O$: C, 60.97; H, 5.00; N, 6.46. Found: C, 60.99; H, 5.26; N, 5.60.

Example 19

1-(2-(2-(5-Methyl-isoxazol-3-yl)-benzofuran-5-yloxy)-ethylamino)-3-phenoxy-propan-2(S)-ol The title compound was prepared by a procedure similar to that described in Example 1.

M.p. 144°–146° C. (acetone).

Analytical calculated for $C_{23}H_{24}N_2O_5$: C, 67.63; H, 5.92; N, 6.86. Found: C, 67.65; H, 5.85; N, 6.73.

Example 20

1-(2-(2-(5-Methyl-isoxazol-3-yl)-benzofuran-5-yloxy)-ethylamino)-3-(2-chloro-phenoxy)-propan-2(S)-ol The title compound was prepared by a procedure similar to that described in Example 1.

M.p. 102°–106° C.

Analytical calculated for $C_{23}H_{23}ClN_2O_5$: C, 62.37; H, 5.23; N, 6.32. Found: C, 62.12; H, 5.58; N, 6.01.

Example 21

1-(2-(2-(5-Methyl-isoxazol-3-yl)-benzofuran-5-yloxy)-ethylamino)-3-(2-fluoro-phenoxy)-propan-2(S)-ol The title compound was prepared by a procedure similar to that described in Example 1.

M.p. 118°–121° C.

Analytical calculated for $C_{23}H_{23}FN_2O_5$: C, 64.78; H, 5.44; N, 6.57. Found: C, 64.97; H, 5.38; N, 6.22.

Example 22

1-(2-(2-Isoxazol-3-yl-benzofuran-5-yloxy)-ethylamino)-3-(2-trifluoromethyl-phenoxy)-propan-2(S)-ol The title compound was prepared by a procedure similar to that described in Example 1.

M.p. 90°–91° C.

Analytical calculated for $C_{23}H_{21}F_3N_2O_5$: C, 59.74; H, 4.58; N, 6.06. Found: C, 59.62; H, 4.49; N, 5.66.

Example 23

1-(2-(2-Isoxazol-3-yl-benzofuran-5-yloxy)-ethylamino)-3-(2-cyano-phenoxy)-propan-2(S)-ol The title compound was prepared by a procedure similar to that described in Example 1.

M.p. 94°–95° C.

Analytical calculated for $C_{23}H_{21}N_3O_5 \cdot 0.5H_2O$: C, 64.57; H, 5.18; N, 9.81. Found: C, 64.26; H, 5.16; N, 9.35.

Example 24

1-(2-(2-Isoxazol-3-yl-benzofuran-5-yloxy)-ethylamino)-3-(2-fluoro-phenoxy)-propan-2(S)-ol The title compound was prepared by a procedure similar to that described in Example 1.

M.p. 109°–110° C.

Analytical calculated for $C_{22}H_{21}FN_2O_5$: C, 64.07; H, 5.13; N, 6.79. Found: C, 63.89; H, 4.98; N, 6.39.

Example 25

1(R)-(3-Chloro-phenyl)-2-(2-(2-isoxazol-3-yl-benzofuran-5-yloxy)-ethylamino)-ethanol The title compound was prepared by a procedure similar to that described in Example 1.

M.p. 112°–120° C.

Analytical calculated for $C_{21}H_{19}ClN_2O_4$: C, 63.24; H, 4.57; N, 7.02. Found: C, 62.94; H, 5.13; N, 5.96.

Example 26

1(R)-(3-Trifluoromethyl-phenyl)-2-(2-(2-isoxazol-3-yl-benzofuran-5-yloxy)-ethylamino)-ethanol The title compound was prepared by a procedure similar to that described in Example 1.

M.p. 113°–114° C.

Analytical calculated for $C_{22}H_{19}F_3N_2O_4$: C, 61.11; H, 4.43; N, 6.48. Found: C, 61.48; H, 4.75; N, 5.79.

Example 27

1(R)-(3-Chloro-phenyl)-2-(2-(2-(5-methyl-isoxazol-3-yl)-benzofuran-5-yloxy)-ethylamino)-ethanol The title compound was prepared by a procedure similar to that described in Example 1.

M.p. 108°–110° C.

Example 28

1(R)-(3-Trifluoromethyl-phenyl)-2-(2-(2-(5-methyl-isoxazol-3-yl)-benzofuran-5-yloxy)-ethylamino)-ethanol The title compound was prepared by a procedure similar to that described in Example 1.

M.p. 126°–127° C.

Analytical calculated for $C_{23}H_{21}F_3N_2O_4$: C, 61.88; H, 4.74; N, 6.27. Found: C, 61.75; H, 4.87; N, 6.20.

EXAMPLE 29

1-(2-(2-(2-Methyl-thiazol-4-yl)-benzofuran-5-yloxy)-ethylamino)-3-phenoxy-propan-2(S)-ol;

The title compound was prepared by a procedure similar to that described in Example 1.

M.p. 150°–152° C.

Example 30

1(R)-(3-Chloro-phenyl)-2-(2-(2-(2-methyl-thiazol-4-yl)-benzofuran-5-yloxy)-ethylamino)-ethanol The title compound was prepared by a procedure similar to that described in Example 1.

M.p. 127°–129° C.

Analytical calculated for $C_{22}H_{21}ClN_2O_3S$: C, 61.60; H, 4.93; N, 6.53. Found: C, 61.54; H, 4.85; N, 6.27.

Example 31

1-(2-(2-(5-Methyl-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 112°–114° C.

Analytical calculated for $C_{22}H_{23}N_3O_5$: C, 64.53; H, 5.66; N, 10.26. Found C, 64.48; H, 5.24; N, 9.97.

Example 32

1-(2-(2-(5-Methyl-(1,2,4)-oxadiazol-3-yl)-benzofuran-5-yloxy)-ethylamino)-3-(2-chloro-phenoxy)-propan-2(S)-ol The title compound was prepared by a procedure similar to that described in Example 1.

M.p. 106°–108° C.

Analytical calculated for $C_{22}H_{22}ClN_3O_5 \cdot 0.2H_2O$: C, 59.04; H, 5.04; N, 9.39. Found: C, 58.79; H, 4.93; N, 9.18.

Example 33

1-(2-(2-(5-Methyl-(1,2,4)-oxadiazol-3-yl)-benzofuran-5-yloxy)-ethylamino)-3-(2-fluoro-phenoxy)-propan-2(S)-ol The title compound was prepared by a procedure similar to that described in Example 1.

M.p. 102.5°–103.5° C.

Analytical calculated for $C_{22}H_{22}FN_3O_5$; C, 61.82; H, 5.19; N, 9.83. Found: C, 61.60; H, 5.21; N, 9.52.

Example 34

1-(2-(2-(5-Trifluoromethyl-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 108°–113° C.

Example 35

1-(2-(2-(5-Trifluoromethyl-(1,2,4)-oxadiazol-3-yl)-benzofuran-5-yloxy)-ethylamino)-3-(2-chloro-phenoxy)-propan-2(S)-ol The title compound was prepared by a procedure similar to that described in Example 1.

M.p. 112°–115° C.

Analytical calculated for $C_{22}H_{19}F_3ClN_3O_5$: C, 53.08; H, 3.85; N, 8.44. Found: C, 53.65; H, 4.08; N, 8.36.

Example 36

1-(2-(2-(5-Trifluoromethyl-(1,2,4)-oxadiazol-3-yl)-benzofuran-5-yloxy)-ethylamino)-3-(2-fluoro-phenoxy)-propan-2(S)-ol The title compound was prepared by a procedure similar to that described in Example 1.

M.p. 117°–119° C.

Analytical calculated for $C_{22}H_{19}F_4N_3O_5$: C, 54.89; H, 3.98; N, 8.73. Found: C, 54.51; H, 3.84; N, 8.38.

Example 37

1-(2-(2-(5-Ethyl-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 97°–98° C.

HRMS Calcd for $C_{23}H_{25}N_3O_5$: 423.1788. Found: 423.1843.

Example 38

1-(2-(2-(5-(2-Propyl)-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 111°–112° C.

Analytical calculated for $C_{24}H_{27}N_3O_5$: C, 65.89; H, 6.22; N, 9.60. Found: C, 65.61; H, 6.15; N, 9.24.

Example 39

1-(2-(2-(5-(2-Phenyl)-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 149°–151° C.

Analytical calculated for $C_{27}H_{25}N_3O_5$: C, 68.78; H, 5.34; N, 8.91. Found: C, 68.98; H, 5.29; N, 8.82.

Example 40

1-(2-(2-(5-(2-(3-Pyridyl))-(1,2,4)-oxadiazol-3-yl)-benzofuran-5-yloxy)-ethylamino)-3-phenoxy-propan-2(S)-ol The title compound was prepared by a procedure similar to that described in Example 1.

M.p. 150°–155° C.

Example 41

1-(2-(2-(1,2,4)-Oxadiazol-3-yl)-benzofuran-5-yloxy)-ethylamino)-3-phenoxy-propan-2(S)-ol The title compound was prepared by a procedure similar to that described in Example 1.

M.p. 118°–119° C.

Analytical calculated for $C_{21}H_{21}N_3O_5$: C, 63.79; H, 5.35; N, 10.63. Found: C, 63.79; H, 5.34; N, 10.62. Found: C, 63.79; H, 5.35; N, 10.63.

Example 42

1-(2(2-(1,2,4)-Oxadiazol-3-yl)-benzofuran-5-yloxy)-ethylamino)-3-(2-chloro-phenoxy)-propan-2(S)-ol The title compound was prepared by a procedure similar to that described in Example 1.

M.p. 102°–104° C.

Analytical calculated for $C_{21}H_{20}ClN_3O_5 \cdot 0.5H_2O$: C, 57.46; H, 4.82; N, 9.57. Found: C, 57.65; H, 4.71; N, 9.07.

Example 43

1-(2-(2-(1,2,4)-Oxadiazol-3-yl)-benzofuran-5-yloxy)-ethylamino)-3-(2-fluoro-phenoxy)-propan-2(S)-ol The title compound was prepared by a procedure similar to that described in Example 1.

M.p. 98°–101° C.

Analytical calculated for $C_{21}H_{20}FN_3O_5$: C, 61.01; H, 4.88; N, 10.16. Found: C, 61.39; H, 4.80; N, 9.01.

Example 44

1(R)-(3-Chloro-phenyl)-2-(2-(2-(5-methyl-(1,2,4)-oxadiazol-3-yl)-benzofuran-5-yloxy)-ethylamino)-ethanol The title compound was prepared by a procedure similar to that described in Example 1.

M.p. 88°–92° C.

Analytical calculated for $C_{21}H_{20}ClN_3O_4$: C, 60.94; H, 4.87; N, 10.15. Found: C, 60.95; H, 4.62; N, 9.75.

Example 45

1(R)-(3-Trifluoro-phenyl)-2-(2-(2-(5-methyl-(1,2,4)-oxadiazol-3-yl)-benzofuran-5-yloxy)-ethylamino)-ethanol The title compound was prepared by a procedure similar to that described in Example 1.

M.p. 96°–98° C.

Analytical calculated for $C_{22}H_{20}F_3N_3O_4$: C, 59.06; H, 4.51; N, 9.39. Found: C, 58.78; H, 4.34; N, 9.17.

Example 46

1(R)-(2-Trifluoromethyl-thiazol-4-yl)-2-(2-(2-(5-methyl-(1,2,4)-oxadiazol-3-yl)-benzofuran-5-yloxy)-ethylamino)-ethanol The title compound was prepared by a procedure similar to that described in Example 1.

M.p. 143°–146° C.

Analytical calculated for $C_{19}H_{17}F_3N_4O_4S$: C, 50.22; H, 3.77; N, 12.33. Found: C, 50.77; H, 3.60; N, 11.67.

Example 47

1(R)-(3-Chloro-phenyl)-2-(2-(2-(5-trifluoromethyl-(1,2,4)-oxadiazol-3-yl)-benzofuran-5-yloxy)-ethylamino)-ethanol The title compound was prepared by a procedure similar to that described in Example 1.

M.p. 108°–111° C.

Analytical calculated for $C_{21}H_{17}F_3ClN_3O_4$: C, 53.92; H, 3.66; N, 8.98. Found: C, 53.93; H, 3.79; N, 8.75.

Example 48

1(R)-(3-Chloro-phenyl)-2-(2-(2-(5-(2-propyl)-(1,2,4)-oxadiazol-3-yl)-benzofuran-5-yloxy)-ethylamino-ethanol The title compound was prepared by a procedure similar to that described in Example 1.

M.p. 84°–87° C.

Analytical calculated for $C_{23}H_{24}ClN_3O_4$: C, 62.51; H, 5.47; N, 9.51. Found C, 62.34; H, 5.35; N, 9.34.

Example 49

1(R)-(3-Chloro-phenyl)-2-(2-(2-(1,2,4)-oxadiazol-3-yl-benzofuran-5-yloxy)-ethylamino)-ethanol The title compound was prepared by a procedure similar to that described in Example 1.

M.p. 103°–105° C.

Analytical calculated for $C_{20}H_{18}ClN_3O_4$: C, 60.08; H, 4.54; N, 10.51. Found: C, 60.19; H, 4.42; N, 9.58.

Example 50

5-(2-(2-(S)-Hydroxy-3-phenoxy-propylamino) ethoxy)-benzofuran-2-carboxylic acid, 1-propyl-amide The title compound was prepared by a procedure similar to that described in Example 4.

M.p. 127°–128° C.

Example 51

(5-(2-(2(S)-Hydroxy-3-phenoxy-propylamino) ethoxy)-benzofuran-2-yl)-pyrrolidin-1-yl-methanone The title compound was prepared by a procedure similar to that described in Example 4.

M.p. 117°–118° C.

Analytical calculated for $C_{24}H_{28}N_2O_5 \cdot 0.2H_2O$: C, 67.34; H, 6.69; N, 6.54. Found: C, 67.11; H, 6.24; N, 6.40.

37

Example 52

(5-(2-(2(S)-Hydroxy-3-(2-chloro-phenoxy)-propylamino)ethoxy)-benzofuran-2-yl)-pyrrolidin-1-yl-methanone The title compound was prepared by a procedure similar to that described in Example 4.

M.p. 89°–90° C.

Analytical calculated for $C_{24}H_{27}ClN_2O_5$: C, 62.80; H, 5.93; N, 6.11. Found: C, 62.59; H, 5.80; N, 5.94.

Example 53

(5-(2-(2(S)-Hydroxy-3-phenoxy-propylamino) ethoxy)-indol-2-yl)-pyrrolidin-1-yl-methanone The title compound was prepared by a procedure similar to that described in Example 4.

M.p. 110°–115° C.

Example 54

(1-Methyl-5-(2-(2-(S)-hydroxy-3-phenoxy-propylamino)ethoxy)-indol-2-yl)-pyrolidin-1-yl-methanone The title compound was prepared by a procedure similar to that described in Example 4.

M.p. 130°–131°0 C.

Analytical calculated for $C_{25}H_{31}N_3O_4 \cdot 0.5H_2O$: C, 67.23; H, 7.22; N, 9.41. Found: C, 67.55; H, 6.98; N, 9.15.

Example 55

5-(2-(2-(3-Chloro-phenyl)-2(R)-hydroxy-ethylamino)-ethoxy)-benzofuran-2-yl)-pyrrolidin-1-yl-methanone The title compound was prepared by a procedure similar to that described in Example 4.

M.p. 96°–98° C.

Analytical calculated for $C_{23}H_{25}ClN_2O_4$: C, 64.41: H, 5.88; N, 6.53. Found: C, 64.41; H, 5.73; N, 6.19.

Example 56

5-(2(R,S)-(2-(2-Trifluoromethyl-thiazol-4-yl)-2(S)-hydroxy-ethylamino)-propyl)-benzofuran-2-carboxylic acid The title compound was prepared by a procedure similar to that described in Example 3.

M.p. 145°–163° C.

Analytical calculated for $C_{18}H_{17}F_3N_2O_4S \cdot 1.25H_2O$: C, 49.48; H, 4.50; N, 6.41. Found: C, 49.38; H, 4.56; N, 6.23.

Example 57

5-(2(R)-(2-(2-Trifluoromethyl-thiazol-4-yl)-2(S)-hydroxy-ethylamino)-propyl)-benzofuran-2-carboxylic acid The title compound was prepared by a procedure similar to that described in Example 3.

M.p. 168°–171° C.

Analytical calculated for $C_{18}H_{17}F_3N_2O_4S \cdot 1.5H_2O$: C, 48.98; H, 4.57; N, 6.35. Found: C, 49.04; H, 4.47; N, 6.06.

38

Example 58

4-(2(R,S)-(2-(2-Trifluoromethyl-thiazol-4-yl)-2-(S)-hydroxy-ethylamino)-propyl)-benzo-furan-2-carboxylic acid The title compound was prepared by a procedure similar to that described in Example 3.

M.p. 158°–176° C.

Analytical calculated for $C_{18}H_{17}F_3N_2O_4S \cdot 1.25H_2O$: C, 48.98; H, 4.57; N, 6.35. Found: C, 48.87; H, 4.31; N, 6.27.

We claim:

1. A method for treating prostate disease in a mammal comprising administering to said mammal a $\beta_3$-adrenoceptor antagonizing or agonizing effective amount of a $\beta_3$-adrenoceptor antagonist or agonist or a pharmaceutically acceptable salt or prodrug thereof.

2. A method of treating a condition selected from the group consisting of intestinal motility disorders, intestinal ulcerations including inflammatory bowel disease, ulcerative colitis, Crohn's disease and proctitis, gastrointestinal ulcerations, depression, prostate disease, and dyslipidemia in a mammal comprising administering to a mammal in need of said treatment an amount of a $\beta_3$-adrenoceptor antagonist or agonist formula

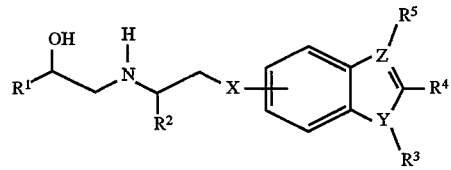

wherein $R^1$ is phenyl, $-(CH_2)_n-$O-phenyl or thiazolyl, wherein said phenyl, the phenyl moiety of said $-(CH_2)_n-$O-phenyl and said thiazolyl may optionally be substituted with one or more substituents, independently selected from hydrogen, $(C_1-C_6)$ alkyl optionally substituted with one or more halo atoms, hydroxy, $(C_1-C_6)$ alkoxy optionally substituted with one or more halo atoms, $(C_1-C_6)$ alkylthio, fluoro, chloro, bromo, iodo, nitro and cyano;

$R^2$ is hydrogen or $(C_1-C_6)$ alkyl optionally substituted with one or more halo atoms;

$R^3$ is hydrogen, $-(CH_2)_n$-phenyl, $-(C_1-C_{10})$ alkyl, $-(CH_2)_n-NR^7R^8$, $-(CH_2)_n-CO_2R^{11}$,

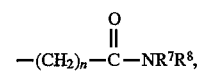

$-(CH_2)_n-OR^{11}$, $-(CH_2)_n-SO_3R^{11}$, $-(CH_2)_n-SO_2-(C_1-C_6)$ alkyl, $-(CH_2)_n-SO_2NR^7R^8$, or a heterocycle selected from $-(CH_2)_n$-pyridyl, $-(CH_2)_n$-pyrimidyl, $-(CH_2)_n$-pyrazinyl, $-(CH_2)_n$-isoxazolyl, $-(CH_2)_n$-oxazolyl, $-(CH_2)_n$-thiazolyl, $-(CH_2)_n$-(1,2,4-oxadiazolyl), $-(CH_2)_n$-imidazolyl, $-(CH_2)_n$-triazolyl and $-(CH_2)_n$-tetrazolyl, wherein one of the ring nitrogen atoms of said $-(CH_2)_n$-imidazolyl, $-(CH_2)_n$-triazolyl or $-(CH_2)_n$-tetrazolyl may optionally be substituted by $(C_1-C_6)$ alkyl optionally substituted with one or more halo atoms, and wherein each of said heterocycles may optionally be substituted on one or more of the ring carbon atoms by $(C_1-C_6)$ alkyl optionally substituted with one or more halo atoms halo, nitro, cyano, $-(CH_2)_n-NR^7R^8$, $-(CH_2)_n-$ $CO_2R^{11}$,

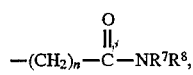

—$(CH_2)_n$—$OR^{11}$, —$(CH_2)_n$—$SO_2R^{11}$, —$(CH_2)_n$—$SO_2$—$(C_1$-$C_6)$ alkyl, or —$(CH_2)_n$—$SO_2NR^7R^8$, and wherein the phenyl moiety of said $(CH_2)_n$-phenyl may optionally be substituted with one or more substituents independently selected from $(C_1$-$C_6)$alkyl optionally substituted with one or more halo atoms hydroxy, $(C_1$-$C_6)$alkoxy optionally substituted with one or more halo atoms, $(C_1$-$C_6)$alkylthio, fluoro, chloro, bromo, iodo, cyano, nitro, —$(CH_2)_n$—$NR^7R^8$, —$(CH_2)_n$—$CO_2R^{11}$,

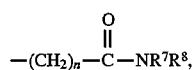

—$(CH_2)_n$—$OR^{11}$, —$(CH_2)_n$—$SO_3R^{11}$, —$(CH_2)_n$—$SO_2$—$(C_1$-$C_6)$alkyl, and —$(CH_2)_n$—$SO_2NR^7R^8$;

$R^4$ is —$(CH_2)_n$—$CN$, —$(CH_2)_n$$CO_2R^{11}$, —$(CH_2)_n$—$SO_3R^{11}$, —$(CH_2)_n$—$SO_2$—$(C_1$-$C_6)$alkyl, —$(CH_2)_n$—$SO_2$—$NR^7R^8$, —$(CH_2)_n$$CH_2OH$ optionally substituted with a suitable protecting group, —$(CH_2)_n$—$CHO$, —$(CH_2)_n$—$C(=O)R^{11}$, —$(CH_2)_n$—$C(=O)NR^7R^8$, or a heterocycle selected from —$(CH_2)_n$-thiazolyl, —$(CH_2)_n$-oxazolyl, —$(CH_2)_n$-imidazolyl, —$(CH_2)_n$-triazolyl, —$(CH_2)_n$-1,2,4-oxadiazolyl, —$(CH_2)_n$-isoxazolyl, —$(CH_2)_n$-tetrazolyl and —$(CH_2)_n$-pyrazolyl; wherein one of the ring nitrogen atoms of said —$(CH_2)_n$-imidazolyl, —$(CH_2)_n$-triazolyl and —$(CH_2)_n$-tetrazolyl may optionally be substituted by $(C_1$-$C_6)$alkyl optionally substituted with one or more halo atoms, wherein each of said heterocycles may optionally be substituted on any of the ring carbon atoms by hydrogen, $(C_1$-$C_6)$alkyl optionally substituted with one or more halo atoms, —$(CH_2)_n$—$NR^7R^8$, —$(CH_2)_n$—$CO_2R^2$, halo, nitro, cyano,

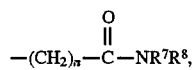

—$(CH_2)_n$—$OR^{11}$, —$(CH_2)_n$—$SO_3R^{11}$, —$(CH_2)_n$—$SO_2$—$(C_1$-$C_6)$alkyl, or —$(CH_2)_n$—$SO_2NR^7R^8$;

$R^5$ is hydrogen or $(C_1$-$C_6)$alkyl optionally substituted with one or more halo atoms;

each $R^7$ and each $R^8$ is selected independently of any other $R^7$ or $R^8$ in the same molecule, and is selected from the group consisting of hydrogen, $(C_1$-$C_6)$alkyl, $(C_1$-$C_8)$alkoxy $(C_1$-$C_6)$alkyl and $(C_3$-$C_8)$cycloalkyl, or $R^7$ and $R^8$, when attached to the same nitrogen atom, together with the nitrogen to which they are attached, form a saturated heterocyclic ring having from 3 to 5 carbon atoms wherein one of said carbon atoms may optionally be replaced by oxygen, nitrogen or sulfur;

$R^{11}$, wherever it occurs, is selected independently from any other $R^{11}$ in the same molecule and is hydrogen or $(C_1$-$C_6)$ alkyl optionally substituted with one or more halo atoms;

n is an integer from zero to six;

X is a direct link, oxygen or sulfur;

Y is oxygen, nitrogen or sulfur; and

Z is carbon or nitrogen;

with the proviso that: (i) when Y is oxygen or sulfur, $R^3$ is absent, and (ii) when Z is nitrogen, $R^5$ is absent;

or a pharmaceutically acceptable prodrug of said compound or a pharmaceutically acceptable salt of said compound or prodrug thereof, that is effective in treating said condition.

3. A method according to claim 2 of treating intestinal motility disorders in a mammal, comprising administering to said mammal in need of such treatment or prevention a $\beta_3$-adrenoceptor antagonizing or agonizing effective amount of a compound of the formula I or a pharmaceutically acceptable prodrug of said compound, or a pharmaceutically acceptable salt of said compound or prodrug thereof, that is effective in treating or preventing said condition.

4. A method according to claim 2 of treating depression, in a mammal, comprising administering to a mammal in need of said treatment or prevention a $\beta_3$-adrenoceptor antagonizing or agonizing effective amount of a compound of the formula I or a pharmaceutically acceptable prodrug of said compound, or a pharmaceutically acceptable salt of said compound or prodrug thereof, that is effective in treating or preventing said condition.

5. A method according to claim 2 of treating prostate disease, in a mammal, comprising administering to a mammal in need of said treatment or prevention a $\beta_3$-adrenoceptor antagonizing or agonizing effective amount of a compound of the formula I or a pharmaceutically acceptable prodrug of said compound, or a pharmaceutically acceptable salt of said compound or prodrug thereof, that is effective in treating or preventing said condition.

6. A method according to claim 2 of treating dyslipidemia, in a mammal, comprising administering to a mammal in need of said treatment or prevention a $\beta_3$-adrenoceptor antagonizing or agonizing effective amount of a compound of the formula I or a pharmaceutically acceptable prodrug of said compound, or a pharmaceutically acceptable salt of said compound or prodrug thereof, that is effective in treating or preventing said condition.

* * * * *